US009669210B2

United States Patent
Barker et al.

(10) Patent No.: US 9,669,210 B2
(45) Date of Patent: Jun. 6, 2017

(54) ELECTRICAL STIMULATION LEADS AND SYSTEMS WITH FOLDING ANCHORING UNITS AND METHODS OF MAKING AND USING

(71) Applicant: BOSTON SCIENTIFIC NEUROMODULATION CORPORATION, Valencia, CA (US)

(72) Inventors: John M. Barker, Ventura, CA (US); David Ernest Wechter, Santa Clarita, CA (US); Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 43 days.

(21) Appl. No.: 14/690,071

(22) Filed: Apr. 17, 2015

(65) Prior Publication Data
US 2015/0297882 A1 Oct. 22, 2015

Related U.S. Application Data

(60) Provisional application No. 62/091,399, filed on Dec. 12, 2014, provisional application No. 61/982,777, filed on Apr. 22, 2014.

(51) Int. Cl.
*A61N 1/00* (2006.01)
*A61N 1/05* (2006.01)
*A61B 17/34* (2006.01)

(52) U.S. Cl.
CPC ............. *A61N 1/0558* (2013.01); *A61N 1/05* (2013.01); *A61B 2017/3484* (2013.01); *A61N 1/057* (2013.01); *A61N 1/0539* (2013.01)

(58) Field of Classification Search
CPC ........ A61N 1/0558; A61N 1/05; A61N 1/056; A61N 1/057; A61N 1/0539; A61B 2017/3484
See application file for complete search history.

(56) References Cited

U.S. PATENT DOCUMENTS 3,754,555 A 8/1973 Schmitt
3,814,104 A 6/1974 Irnich
(Continued)

FOREIGN PATENT DOCUMENTS

WO 2004028618 4/2004
WO 2005028023 3/2005
(Continued)

OTHER PUBLICATIONS

U.S. Appl. No. 62/006,824, filed Jun. 2, 2014.
U.S. Appl. No. 14/634,253, filed Feb. 27, 2015.
U.S. Appl. No. 62/111,596, filed Feb. 3, 2015.

*Primary Examiner* — Lindsey G Wehrheim
(74) *Attorney, Agent, or Firm* — Lowe Graham Jones PLLC; Bruce E. Black

(57) ABSTRACT

An electrical stimulation lead includes at least one anchoring unit and each anchoring unit includes a lead attachment element. Some anchoring units include one or more anchoring fins attached to the lead attachment element and extending away from the lead attachment element when in a deployed position for contact with patient tissue to anchor the lead within the patient tissue. Each anchoring fin also has a retracted position in which the anchoring fin folds down and lies next to the lead attachment element. Other anchoring units include one or more anchoring tabs defined by the lead attachment element. Each anchoring tab is partially separated from a remainder of the lead attachment element by at least one cutout and extends away from the remainder of the lead attachment element when in a deployed position for contact with patient tissue to anchor the lead within the patient tissue.

18 Claims, 13 Drawing Sheets

(56) References Cited

U.S. PATENT DOCUMENTS

| | | | |
|---|---|---|---|
| 4,112,952 | A | 9/1978 | Thomas et al. |
| 4,280,512 | A | 7/1981 | Karr et al. |
| 4,378,023 | A | 3/1983 | Trabucco |
| 4,407,303 | A * | 10/1983 | Akerstrom ............ A61N 1/057 607/126 |
| 4,519,404 | A | 5/1985 | Fleischhacker |
| 4,706,682 | A | 11/1987 | Stypulkowski et al. |
| 4,721,118 | A * | 1/1988 | Harris .................. A61N 1/057 607/128 |
| 4,913,147 | A | 4/1990 | Fahlstrom et al. |
| 5,052,407 | A | 10/1991 | Hauser et al. |
| 5,314,462 | A | 5/1994 | Heil, Jr. et al. |
| 5,325,870 | A | 7/1994 | Kroll et al. |
| 5,374,279 | A * | 12/1994 | Duffin, Jr. ............... A61N 1/05 607/37 |
| 5,466,255 | A | 11/1995 | Franchi |
| 5,492,119 | A | 2/1996 | Abrams |
| 5,507,802 | A | 4/1996 | Imran |
| 5,571,162 | A | 11/1996 | Lin |
| 5,609,623 | A | 3/1997 | Lindegren |
| 5,674,273 | A | 10/1997 | Helland |
| 5,824,030 | A * | 10/1998 | Yang ...................... A61N 1/056 600/374 |
| 5,868,741 | A | 2/1999 | Chia et al. |
| 5,871,532 | A | 2/1999 | Schroeppel |
| 5,922,014 | A | 7/1999 | Warman et al. |
| 5,948,014 | A | 9/1999 | Valikai |
| 5,957,966 | A | 9/1999 | Schroeppel et al. |
| 6,093,185 | A | 7/2000 | Ellis et al. |
| 6,181,969 | B1 | 1/2001 | Gord |
| 6,181,973 | B1 * | 1/2001 | Ceron .................... A61N 1/057 607/126 |
| 6,249,708 | B1 | 6/2001 | Nelson et al. |
| 6,345,198 | B1 | 2/2002 | Mouchawar et al. |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,671,544 | B2 | 12/2003 | Baudino |
| 6,741,892 | B1 | 5/2004 | Meadows et al. |
| 6,999,819 | B2 | 2/2006 | Swoyer et al. |
| 7,130,700 | B2 | 10/2006 | Gardeski et al. |
| 7,187,983 | B2 | 3/2007 | Dahlberg et al. |
| 7,244,150 | B1 | 7/2007 | Brase et al. |
| 7,328,068 | B2 | 2/2008 | Spinelli et al. |
| 7,343,202 | B2 | 3/2008 | Mrva et al. |
| 7,369,894 | B2 | 5/2008 | Gerber |
| 7,437,193 | B2 | 10/2008 | Parramon et al. |
| 7,565,198 | B2 | 7/2009 | Bennett et al. |
| 7,672,734 | B2 | 3/2010 | Anderson et al. |
| 7,761,165 | B1 | 7/2010 | He et al. |
| 7,835,801 | B1 | 11/2010 | Sundararajan et al. |
| 7,881,783 | B2 | 2/2011 | Bonde et al. |
| 7,899,550 | B1 | 3/2011 | Doan et al. |
| 7,927,282 | B2 | 4/2011 | Hettrick et al. |
| 7,949,395 | B2 | 5/2011 | Kuzma |
| 7,974,706 | B2 | 7/2011 | Moffitt et al. |
| 8,096,959 | B2 | 1/2012 | Stewart et al. |
| 8,175,710 | B2 | 5/2012 | He |
| 8,224,450 | B2 | 7/2012 | Brase |
| 8,364,278 | B2 | 1/2013 | Pianca et al. |
| 8,452,420 | B2 | 5/2013 | Flach et al. |
| 8,469,954 | B2 | 6/2013 | Young et al. |
| 8,532,789 | B2 | 9/2013 | Smits |
| 2002/0151867 | A1 | 10/2002 | McGuckin, Jr. et al. |
| 2002/0156058 | A1 | 10/2002 | Borkan |
| 2003/0195600 | A1 | 10/2003 | Tronnes et al. |
| 2004/0116992 | A1 | 6/2004 | Wardle et al. |
| 2004/0230279 | A1 | 11/2004 | Cates et al. |
| 2005/0288722 | A1 | 12/2005 | Eigler et al. |
| 2007/0043414 | A1 | 2/2007 | Fifer et al. |
| 2007/0049980 | A1 | 3/2007 | Zielinski et al. |
| 2007/0150036 | A1 | 6/2007 | Anderson |
| 2007/0179583 | A1 * | 8/2007 | Goetzinger ........ A61B 17/3468 607/126 |
| 2007/0293923 | A1 | 12/2007 | Soltis et al. |
| 2008/0103569 | A1 | 5/2008 | Gerber |
| 2008/0103572 | A1 | 5/2008 | Gerber |
| 2008/0167701 | A1 | 7/2008 | John et al. |
| 2008/0183253 | A1 | 7/2008 | Bly |
| 2008/0183266 | A1 | 7/2008 | D'Aquanni et al. |
| 2009/0012592 | A1 | 1/2009 | Buysman et al. |
| 2009/0054949 | A1 | 2/2009 | Alexander et al. |
| 2009/0248095 | A1 | 10/2009 | Schleicher et al. |
| 2009/0254151 | A1 | 10/2009 | Anderson et al. |
| 2010/0131036 | A1 | 5/2010 | Geistert et al. |
| 2010/0168806 | A1 | 7/2010 | Norlin-Weissenrieder et al. |
| 2010/0256696 | A1 | 10/2010 | Schleicher et al. |
| 2011/0251662 | A1 | 10/2011 | Griswold et al. |
| 2011/0313427 | A1 * | 12/2011 | Gindele ............... A61N 1/0558 606/129 |
| 2012/0053665 | A1 | 3/2012 | Stolz et al. |
| 2012/0323253 | A1 | 12/2012 | Garai et al. |
| 2013/0066411 | A1 | 3/2013 | Thacker et al. |
| 2013/0218127 | A1 * | 8/2013 | Rosenberg ............ A61M 5/158 604/506 |
| 2014/0330287 | A1 | 11/2014 | Thompson-Nauman et al. |
| 2014/0343645 | A1 | 11/2014 | Wechter |
| 2014/0343656 | A1 | 11/2014 | Wechter |
| 2015/0039069 | A1 | 2/2015 | Rys et al. |
| 2015/0051616 | A1 | 2/2015 | Haasl et al. |

FOREIGN PATENT DOCUMENTS

| | | |
|---|---|---|
| WO | 2013082283 | 6/2013 |
| WO | 2015167800 | 11/2015 |

* cited by examiner

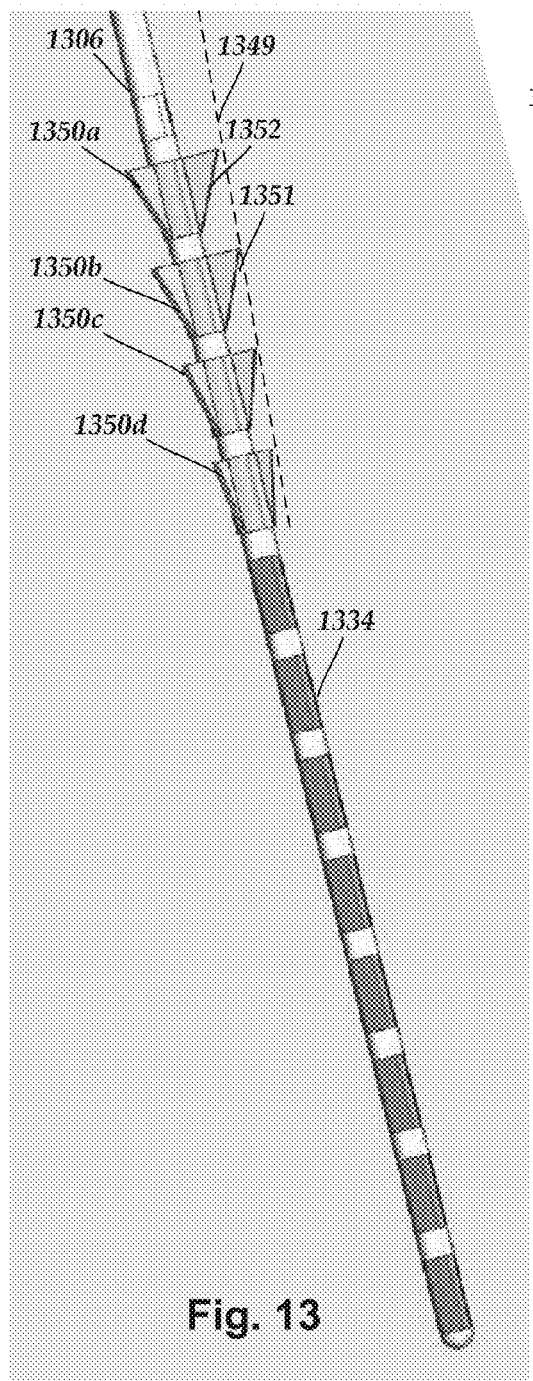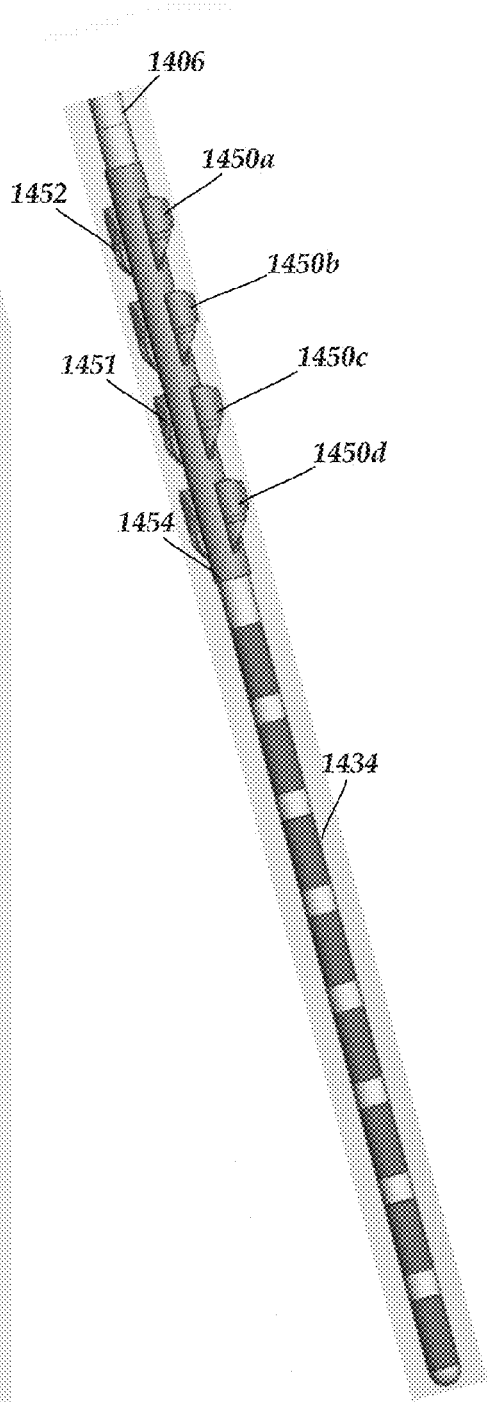
Fig. 13
Fig. 14

ELECTRICAL STIMULATION LEADS AND SYSTEMS WITH FOLDING ANCHORING UNITS AND METHODS OF MAKING AND USING

CROSS-REFERENCE TO RELATED APPLICATIONS

This application claims the benefit under 35 U.S.C. §119 (e) of U.S. Provisional Patent Application Ser. No. 62/091,399 filed Dec. 12, 2014, and U.S. Provisional Patent Application Ser. No. 61/982,777, filed Apr. 22, 2014, both of which are incorporated herein by reference.

FIELD

The present invention is directed to the area of implantable electrical stimulation systems and methods of making and using the systems, and in particular implantable electrical stimulation leads having anchoring units and methods of making and using the leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

One concern regarding implanted leads is lead migration. This may occur over time and result in movement of the lead away from the desired tissue for stimulation so as to reduce the effectiveness of therapeutic treatment.

BRIEF SUMMARY

One embodiment is an electrical stimulation lead including a lead body having a distal end portion, a proximal end portion, and a longitudinal length; electrodes disposed along the distal end portion of the lead body; terminals disposed along the proximal end portion of the lead body; conductors electrically coupling the terminals to the electrodes; and at least one anchoring unit disposed along the lead body, each anchoring unit having a first end and a second end. Each anchoring unit includes a lead attachment element and at least one anchoring fin. Each anchoring fin is attached to the lead attachment element and extends away from the lead attachment element when in a deployed position and is configured and arranged for contact with patient tissue to anchor the lead within the patient tissue. Each anchoring fin is configured and arranged to have a retracted position in which the anchoring fin folds down and lies next to the lead attachment element and does not overlap with any other of the anchoring fins in the retracted position.

In some instances, each anchoring fin increases in size from the first end to the second end of the at least one anchoring unit or each anchoring fin has a curled distal end. In some instances, at least one anchoring fin extends normal to the lead attachment element in the deployed state. In some instances, each anchoring fin has a first side and the first side of at least one of the anchoring fins forms an angle with the lead attachment element of less than 90 degree so that the anchoring fin preferentially folds down with the first side next to the lead attachment element. In some instances, at least one anchoring fin has a first end and a second end and extends from the first end to the second end of the anchoring fin along a line that is not parallel to the central axis of the central lumen. In some instances, at least one anchoring fin has a first end and a second end and extends from the first end to the second end of the anchoring fin along a non-linear curve. In some instances, each anchoring fin is coupled in a curved attachment along the lead attachment element. In some instances, the lead attachment element is part of the lead body. In some instances, the at least one anchoring unit is multiple anchoring units and either the anchoring elements of adjacent anchoring units are rotationally staggered or the outer diameter of the anchoring elements decreases between adjacent anchoring units.

Another embodiment is an electrical stimulation lead including a lead body having a distal end portion, a proximal end portion, and a longitudinal length; electrodes disposed along the distal end portion of the lead body; terminals disposed along the proximal end portion of the lead body; conductors electrically coupling the terminals to the electrodes; and at least one anchoring unit disposed along the lead body, each anchoring unit having a first end and a second end. Each anchoring unit includes a lead attachment element defining at least one anchoring tab. Each anchoring tab is partially separated from a remainder of the lead attachment element by at least one cutout and extends away from the remainder of the lead attachment element when in a deployed position for contact with patient tissue to anchor the lead within the patient tissue. Each anchoring tab is configured and arranged to have a retracted position in which the at least one anchoring tab form a cylindrical arrangement with the remainder of the lead attachment element. In some instances, the lead attachment element is part of the lead body.

Yet another embodiment is an electrical stimulation system that includes any one of the electrical stimulation lead described above and a control module coupleable to the electrical stimulation lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 13 is a schematic side view of another embodiment of a portion of a lead with lead anchoring units disposed between electrodes and with tapering outer diameter, according to the invention; and FIG. 14 is a schematic side view of another embodiment of a portion of a lead with lead anchoring units disposed between electrodes and with curling of the distal ends of the anchoring elements, according to the invention.

DETAILED DESCRIPTION

The present invention is directed to the area of implantable electrical stimulation systems and methods of making and using the systems, and in particular implantable electrical stimulation leads having anchoring units and methods of making and using the leads.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
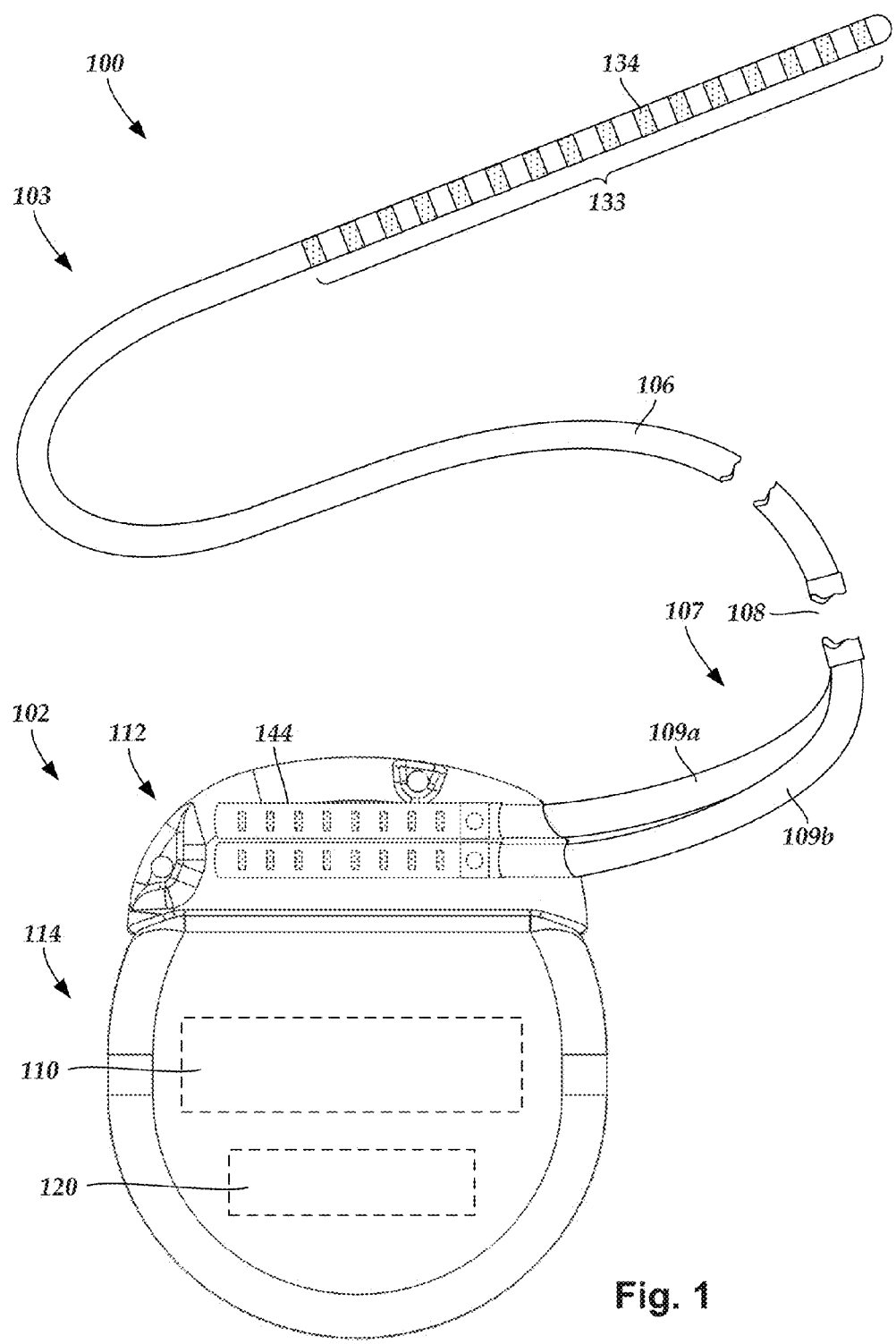
FIG. 1 is a schematic view of one embodiment of an electrical stimulation system that includes a lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation; neural stimulation; spinal cord stimulation; muscle stimulation; neurostimulation to treat one or more of overactive bladder, urinary incontinence, fecal incontinence, or other bladder/bowel conditions; and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
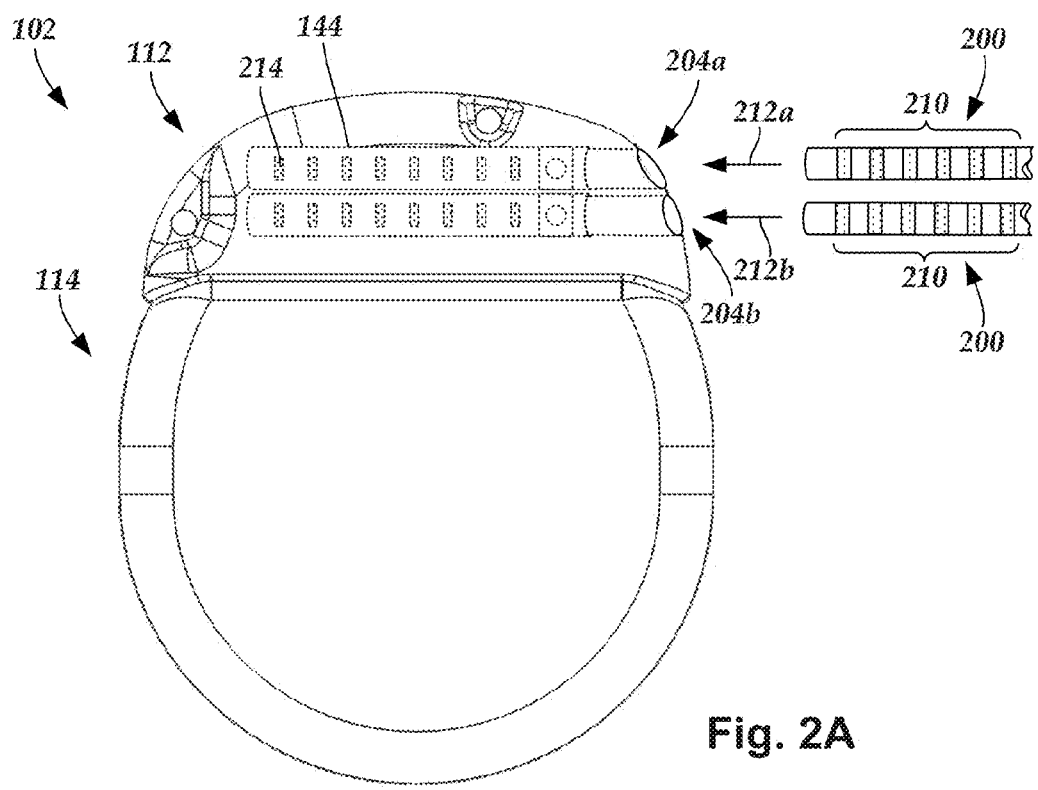
FIG. 2A is a schematic view of one embodiment of the control module of FIG. 1 configured and arranged to electrically couple to an elongated device, according to the invention.
Figure 2B:
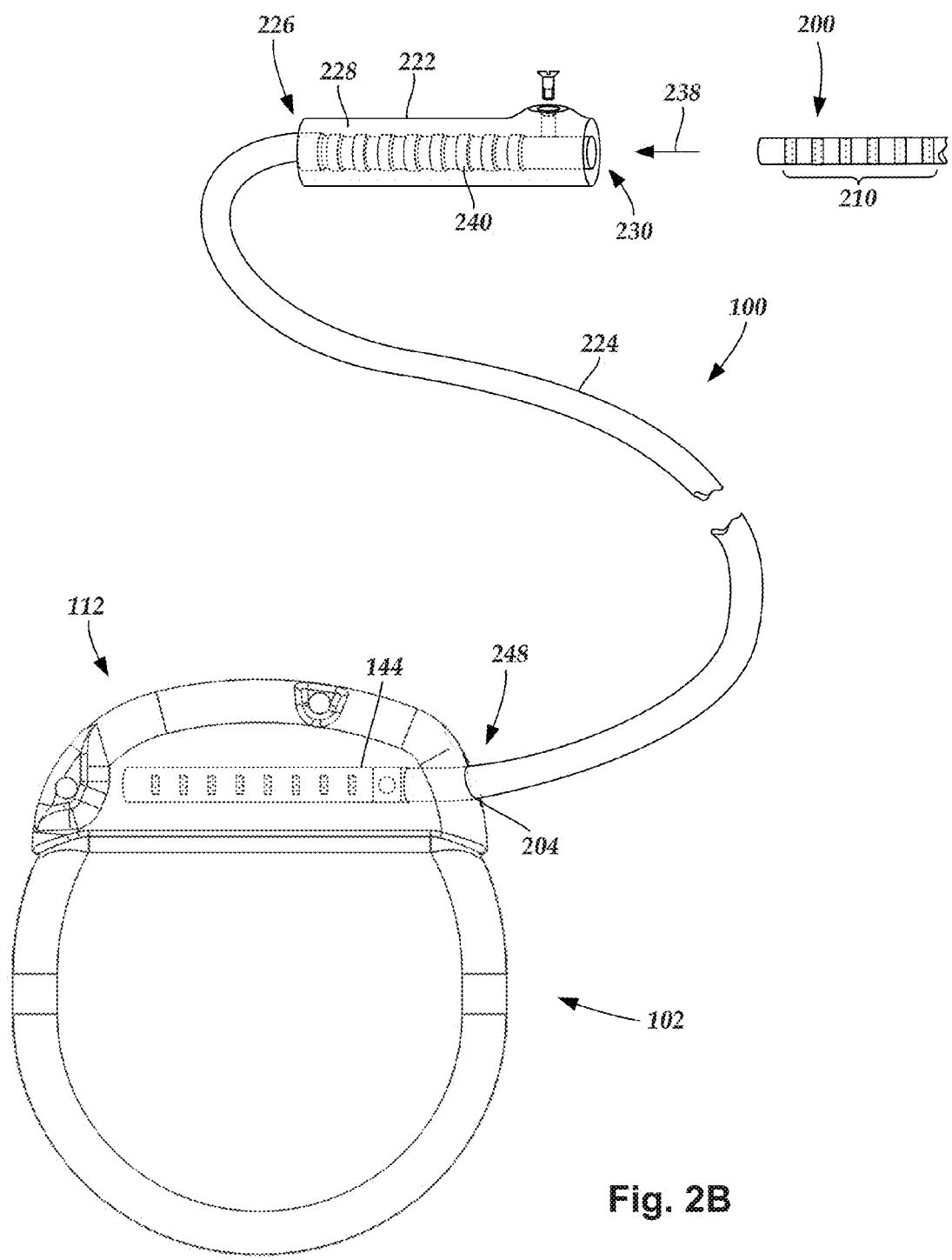
FIG. 2B is a schematic view of one embodiment of a lead extension configured and arranged to electrically couple the elongated device of FIG. 2A to the control module of FIG. 1, according to the invention.

Terminals (e.g., 210 in FIGS. 2A-2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIG. 2A and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Lead anchoring units can be attached to the lead to facilitate anchoring the lead into patient tissue. The term "tissue" includes, but is not limited to, muscular tissue, connective tissue, organ tissue, bone, cartilage, nerve tissue, and the like. These lead anchoring units, as opposed to conventional lead anchors, can be delivered with the lead through an introducer during the implantation process. The lead anchoring units include anchoring elements that lodge against patient tissue and prevent or reduce lateral or axial (or both lateral and axial) migration of the lead after implantation. The lead anchoring units can be particularly useful for leads for sacral nerve stimulation, spinal cord stimulation, or the stimulation of other patient tissue and organs. The lead anchoring units can be positioned anywhere along the lead. The embodiments described below indicate positioning of the lead anchoring units along the distal end portion of the lead body, but it will be understood that the lead anchoring units can be positioned along the proximal end portion or anywhere between the proximal end portion or the distal end portion, or in any combination of positions when multiple lead anchoring units are employed.

Figure 3A:
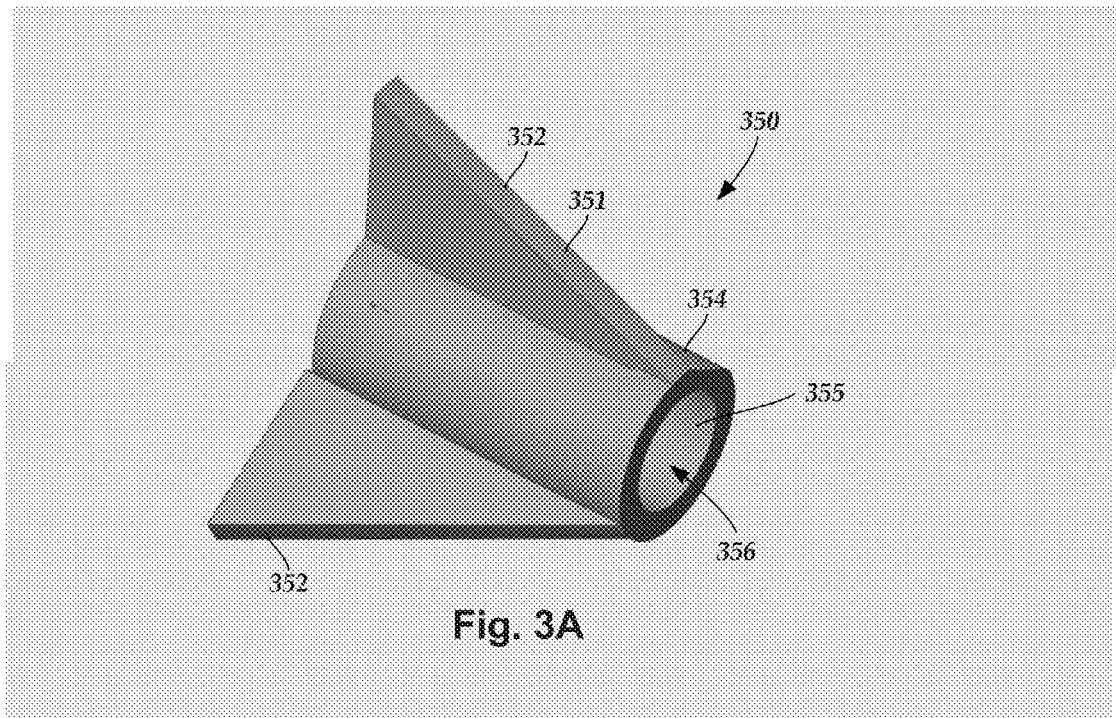
FIG. 3A is a schematic perspective view of one embodiment of a lead anchoring unit in a deployed position, according to the invention.
Figure 3B:
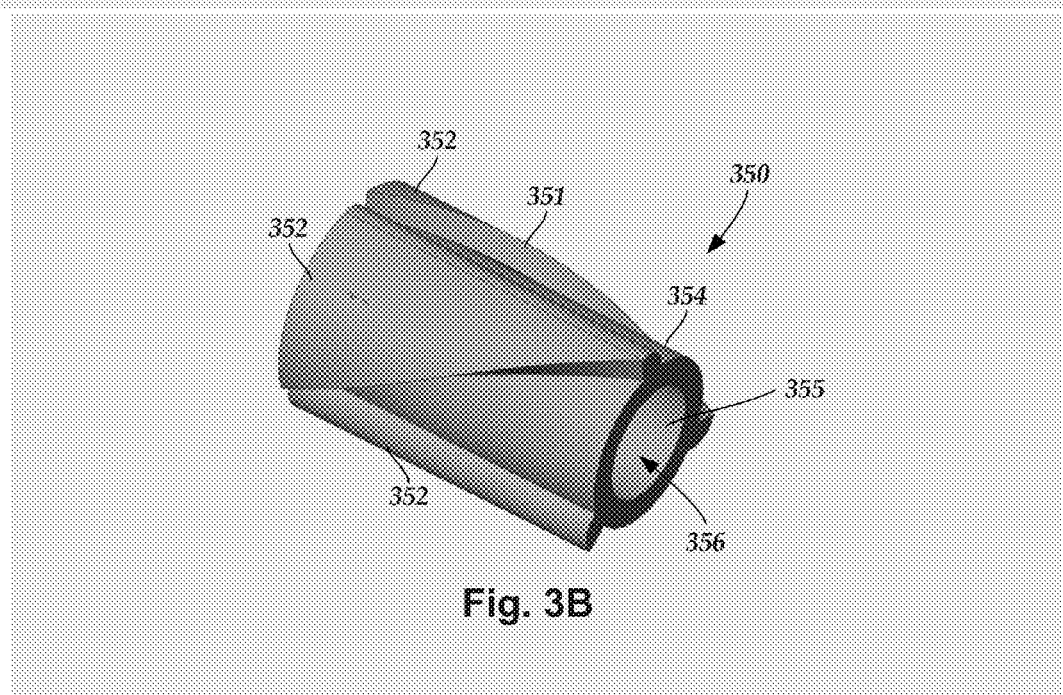
FIG. 3B is a schematic perspective view of the lead anchoring unit of FIG. 3A in a retracted position, according to the invention.

FIGS. 3A and 3B illustrate one embodiment of a lead anchoring unit 350 that can be disposed along a distal end portion of a lead body (e.g., the lead body 106 as shown in FIG. 1). The lead anchoring unit facilitates anchoring the lead body to the surrounding tissue when implanted within a patient's body.

The anchoring unit 350 includes a lead attachment element 354 having a tube-shaped (e.g., cylindrical) configuration. As shown, the lead attachment element 354 has a central lumen 356 extending along the length of the lead attachment element. The central lumen 356 fits around at least a portion of the lead body of a lead. In at least some embodiments, the lead attachment element 354 has a circular cross-section. However, the lead attachment element 354 can be formed of any other suitable shape, including shapes having an elliptical, rectangular, polygonal, irregular, or any other suitable lateral cross-section. The lead attachment element 354 can have a uniform lateral cross-section along its entire length or a varying lateral cross-section along its length.

In at least some embodiments, the cross-section and dimensions of the lead attachment element 354 are dictated by the configuration of the lead body. In at least some embodiments, the outer diameter of the lead body may be slightly larger than the diameter of the central lumen 356 so that the lead attachment element fits snuggly on the lead body.

In other embodiments, the outer diameter of the lead body at the anchor attachment site can be reduced by, for example, grinding, cutting, heating the lead body to flow material of the lead body away from the heated section and form a smaller outer diameter, or the like. The central lumen 356 of the lead attachment element 354 may then be expanded using heat or chemicals and the lead anchor unit 350 slid onto the lead to the anchor attachment site. In at least some of these embodiments, the diameter of the central lumen 356 is equal to or less than the outer diameter of the lead body adjacent the anchor attachment site (i.e., the outer diameter of the lead body before reduction at the anchor attachment site). These methods for attaching the anchoring unit to the lead body can be utilized with any of the anchoring units described herein.

The anchoring unit 350 includes at least one anchoring element 352 coupled to the lead attachment element 354. The anchoring element(s) 352 are disposed around the lead attachment element 354 and extend away from the lead attachment element 354 when in a deployed position, as illustrated in FIG. 3A. In the illustrated embodiment, the anchoring elements 352 are anchoring fins 351. Any number of fins (or other anchoring elements) can be used. The embodiment shown in FIGS. 3A and 3B includes three fins 351 disposed about the circumference of the lead attachment element 354. The fins 351 shown in FIGS. 3A and 3B have a triangular-shaped configuration (e.g., a right triangular shape), but it will be recognized that the fins 351 can have any suitable shape including, but not limited to, trapezoidal, rectangular, regular, irregular, and the like. The triangular-shaped (or ramped or angled) arrangement in FIGS. 3A and 3B can facilitate easier insertion into or out of an introducer, depending in part on the direction the angled portion is facing. As illustrated in FIG. 3A, in at least some embodiments, the fins 351 increase in size (e.g., area or distance extending away from lead attachment element 354) towards the proximal end of the lead moving from one end of the lead attachment element to the other end.

Figure 3C:
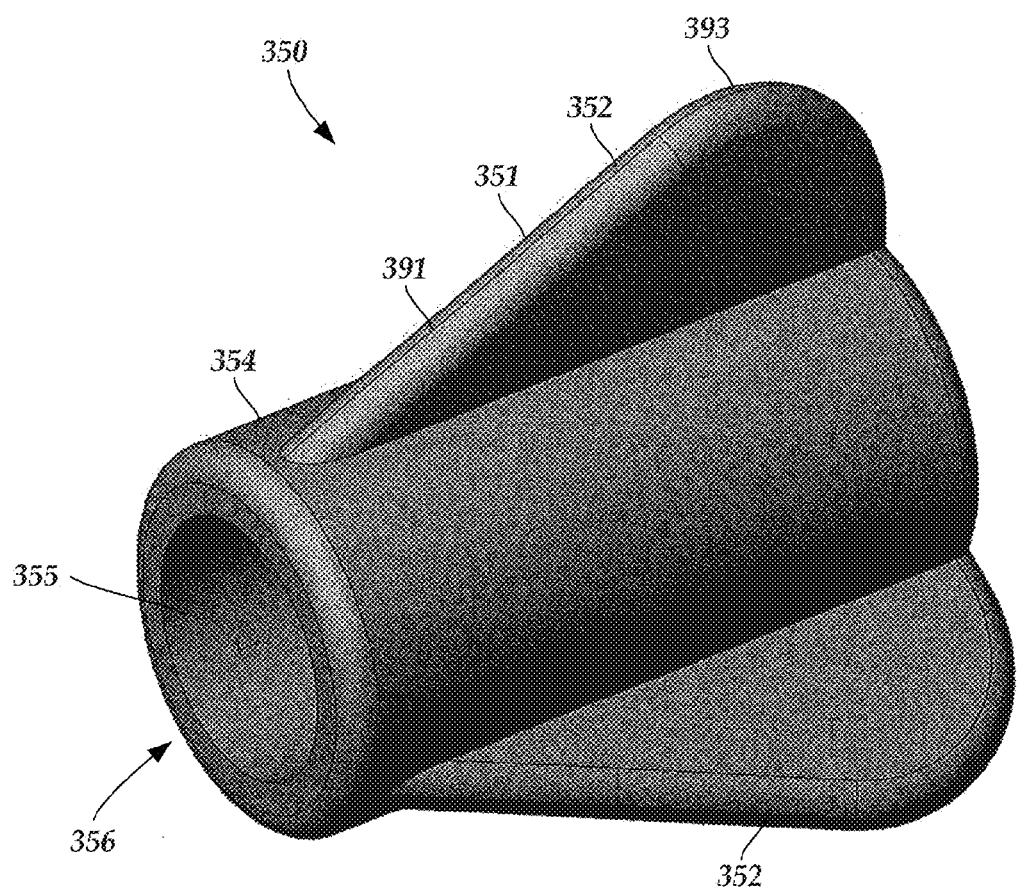
FIG. 3C is a schematic perspective view of an alternative fin arrangement for the lead anchoring unit of FIG. 3A with the edges and tip of the fin curved to reduce sharp edges, according to the invention.

FIG. 3C illustrates another arrangement of fins 352 in which the edges 391 of the fins are radiused (e.g., curved) and the tip 393 of the fin is also radiused (e.g., curved) to reduce the sharp edges. Such radiusing or curving of the edges, tip, or both can be used with any of the anchoring units described herein.

Any suitable number of fins may be disposed about the circumference of the lead attachment element 354 including, but not limited to, two, three, four, five, six, seven, eight, or more fins. The fins can be spaced apart uniformly or non-uniformly around the circumference of the lead attachment element 354. In some embodiments, when deployed the fins 351 form an angle of ninety degrees with (or is normal to) the lead attachment element, as illustrated in FIG. 3A.

The fins 351 are shown in FIG. 3A as extending along a full length of the lead attachment element 354, while being disposed about the circumference of the lead attachment element 354. However, in other embodiments, the fins 351 can extend along only a part (for example, 95%, 90%, 75%, 50%, or less) of the length of the lead attachment element 354.

The fins 351 are arranged to fold down and, at least in some embodiments, lie next to the lead attachment element 354 in a retracted position, as illustrated in FIG. 3B. The fins 351 do not overlap each other when folded down into the retracted position. The retracted position is useful for implantation by delivery of the lead, with one or more anchoring units 350 attached, through an introducer, such as a needle, sheath, or cannula or any other suitable introducer. When the lead is inserted into the introducer, the fins 351 can fold down into the retracted position to reduce the overall diameter of the arrangement to no greater than the inner diameter of the introducer. The fins 351 do not overlap to minimize or reduce the resulting diameter of the arrangement in the retracted position. When the lead is implanted, the introducer is removed allowing the fins to extend into the deployed position, illustrated in FIG. 3A.

In at least some embodiments, the fins 351 are arranged to preferentially extend in the deployed position unless constrained by, for example, the introducer. In some embodiments, deployment may be assisted or completed by action of a user. In some embodiments, the fins 351 may be deployed into the deployed position, after withdrawal of the introducer, by rotating the lead (for example, by one quarter turn, one third turn, one half turn, or one full turn), pulling the lead backward, pushing the lead forward, or any combination of these movements or any other suitable movement (or combination of movements) of the lead. Alternatively, other methods or mechanisms for deploying the fins can also be used.

In at least some embodiments, an interior surface 355 of the lead attachment element 354 may be patterned to assist in maintaining the position of the lead anchoring unit on the lead. The pattern may be regular or irregular and may include features, such as, but not limited to, surface roughening, cutouts, grooves, regular or irregular shapes, or the like. In at least some embodiments, an outer surface of the lead body 106 may be patterned. The pattern may be regular or irregular and may include features, such as, but not limited to, surface roughening, cutouts, grooves, regular or irregular shapes, or the like. In some embodiments, both the interior surface of the lead attachment element and the outer surface of the lead body are patterned. The patterning of the lead attachment element and the lead body may be complementary. In at least some embodiments, the pattern on the interior surface of the lead attachment element and the pattern on the exterior surface of the lead body can be generated so that the two patterns interlock with each other. The patterning described above may be formed using any suitable method, including, but not limited to, ablation (e.g., RF or laser ablation), grinding, knurling, chemical etching, or the like.

Figure 4:
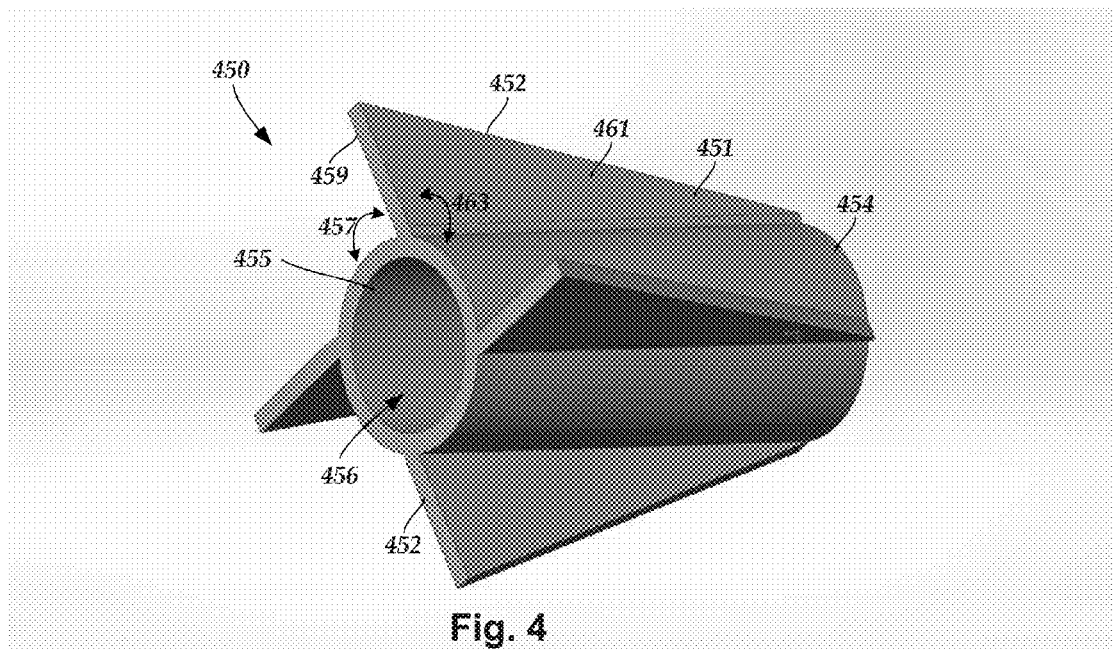
FIG. 4 is a schematic perspective view of a second embodiment of a lead anchoring unit in a deployed position, according to the invention.

FIG. 4 illustrates another embodiment of a lead anchoring unit 450 that can be disposed along a distal end portion of a lead body (e.g., the lead body 106 as shown in FIG. 1). The lead anchoring unit facilitates anchoring the lead body to the surrounding tissue when implanted within a patient's body. The elements of lead anchoring unit 450 are the same as similarly named elements of lead anchoring unit 350 except as described below.

The anchoring unit 450 includes a lead attachment element 454 having a tube-shaped (e.g., cylindrical) configuration. As shown, the lead attachment element 454 has a central lumen 456 extending along the length of the lead attachment element and having an interior surface 455. The central lumen 456 fits around at least a portion of the lead body of a lead. In at least some embodiments, the lead attachment element 454 has a circular cross-section. However, the lead attachment element 454 can be formed of any other suitable shape, including shapes having an elliptical, rectangular, polygonal, irregular, or any other suitable lateral cross-section. The lead attachment element 454 can have a uniform lateral cross-section along its entire length or a varying lateral cross-section along its length. In at least some embodiments, the cross-section and dimensions of the lead attachment element 454 are dictated by the configuration of the lead body. In at least some embodiments, the outer diameter of the lead body may be slightly larger than the diameter of the central lumen 456 so that the lead attachment element fits snuggly on the lead body.

The anchoring unit 450 includes at least one anchoring element 452 coupled to the lead attachment element 454. The anchoring element(s) 452 are disposed around the lead attachment element 454 and extend away from the lead attachment element 454 when in a deployed position, as illustrated in FIG. 4. In the illustrated embodiment, the anchoring elements 452 are anchoring fins 451. Any number of fins (or other anchoring elements) can be used. The embodiment shown in FIG. 4 includes four fins 451 disposed about the circumference of the lead attachment element 454. The fins 451 shown in FIG. 4 have a triangular-shaped configuration (e.g., a right triangular shape), but it will be recognized that the fins 451 can have any suitable shape including, but not limited to, trapezoidal, rectangular, regular, irregular, and the like. The triangular-shaped (or ramped or angled) arrangement in FIG. 4 can facilitate easier insertion into or out of an introducer, depending in part on the direction the angled portion is facing. Any suitable number of fins may be disposed about the circumference of the lead attachment element 454 including, but not limited to, two, three, four, five, six, seven, eight, or more fins. The fins can be spaced apart uniformly or non-uniformly around the circumference of the lead attachment element 454.

This embodiment differs from that illustrated in FIGS. 3A and 3B in that one side 459 of each fin 452 forms an angle 457 of less than ninety degrees with the lead attachment element, as illustrated in FIG. 4. It will be recognized that the fins could extend at any suitable angle less than ninety degrees from (or not normal to) the lead attachment element (for example, an angle in the range from 30 to 87 degrees or in the range from 60 to 87 degrees or in the range from 75 to 85 degrees or in the range from 50 to 80 degrees.) In at least some embodiments, the other side 461 of the fin 452 makes an angle 463 of more than ninety degrees with the lead attachment. In at least some embodiments, the angles 457 and 463 are complementary angles and add to 180 degrees or approximately 180 degrees.

The fins 451 are shown in FIG. 4 as extending along a full length of the lead attachment element 454, while being disposed about the circumference of the lead attachment element 454. However, in other embodiments, the fins 451 can extend along only a part (for example, 95%, 90%, 75%, 50%, or less) of the length of the lead attachment element 454.

The fins 451 are arranged to fold down and, at least in some embodiments, lie next to the lead attachment element 454 in a refracted position (not shown, but similar to the arrangement illustrated in FIG. 3B). The fins 451 do not overlap each other when folded down into the retracted position. The refracted position is useful for implantation by delivery of the lead, with one or more anchoring units 450 attached, through an introducer, such as a needle, sheath, or cannula or any other suitable introducer. When the lead is inserted into the introducer, the fins 451 can fold down into the retracted position to reduce the overall diameter of the arrangement to no greater than the inner diameter of the introducer. In at least some embodiments, the fins 451 do not overlap to minimize or reduce the resulting diameter of the arrangement in the retracted position. The arrangement of the fins 451 facilitates folding of the fin downward in a preferential direction (e.g., in the direction of the angle 457 of less than ninety degrees.) In at least some embodiments, this preferential folding places side 459 next to, or near, the lead attachment element 454 when the fin 451 is in the retraction position.

When the lead is implanted, the introducer is removed allowing the fins to extend into the deployed position, illustrated in FIG. 4. In at least some embodiments, the fins 451 are arranged to preferentially extend in the deployed position unless constrained by, for example, the introducer. In some embodiments, the fins 451 may be deployed into the deployed position, after withdrawal of the introducer, by rotating the lead (for example, by one quarter turn, one third turn, one half turn, or one full turn), pulling the lead backward, pushing the lead forward, or any combination of these movements or any other suitable movement (or combination of movements) of the lead. Alternatively, other methods or mechanisms for deploying the fins can also be used.

Figure 5:
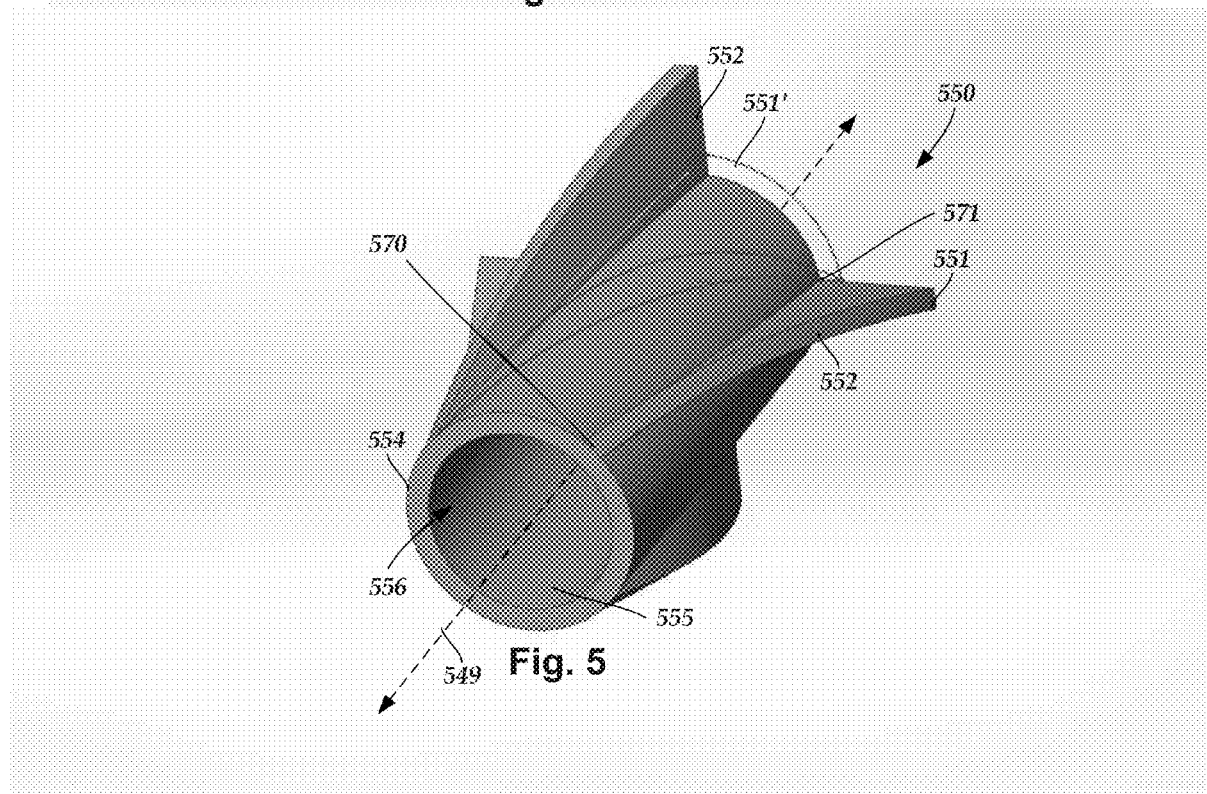
FIG. 5 is a schematic perspective view of a third embodiment of a lead anchoring unit in a deployed position with the outline of one fin in a retracted position, according to the invention.

FIG. 5 illustrates another embodiment of a lead anchoring unit 550 that can be disposed along a distal end portion of a lead body (e.g., the lead body 106 as shown in FIG. 1). The lead anchoring unit facilitates anchoring the lead body to the surrounding tissue when implanted within a patient's body.

The elements of lead anchoring unit 550 are the same as similarly named elements of lead anchoring unit 350 except as described below.

The anchoring unit 550 includes a lead attachment element 554 having a tube-shaped (e.g., cylindrical) configuration. As shown, the lead attachment element 554 has a central lumen 556 extending along the length of the lead attachment element and having an interior surface 555. The central lumen 556 fits around at least a portion of the lead body of a lead. In at least some embodiments, the lead attachment element 554 has a circular cross-section. However, the lead attachment element 554 can be formed of any other suitable shape, including shapes having an elliptical, rectangular, polygonal, irregular, or any other suitable lateral cross-section. The lead attachment element 554 can have a uniform lateral cross-section along its entire length or a varying lateral cross-section along its length. In at least some embodiments, the cross-section and dimensions of the lead attachment element 554 are dictated by the configuration of the lead body. In at least some embodiments, the outer diameter of the lead body may be slightly larger than the diameter of the central lumen 556 so that the lead attachment element fits snuggly on the lead body.

The anchoring unit 550 includes at least one anchoring element 552 coupled to the lead attachment element 554. The anchoring element(s) 552 are disposed around the lead attachment element 554 and extend away from the lead attachment element 554 when in a deployed position, as illustrated in FIG. 5. In the illustrated embodiment, the anchoring elements 552 are anchoring fins 551. Any number of fins (or other anchoring elements) can be used. The embodiment shown in FIG. 5 includes four fins 551 disposed about the circumference of the lead attachment element 554. The fins 551 shown in FIG. 5 have a triangular-shaped configuration (e.g., a right triangular shape), but it will be recognized that the fins 551 can have any suitable shape including, but not limited to, trapezoidal, rectangular, regular, irregular, and the like. The triangular-shaped (or ramped or angled) arrangement in FIG. 5 can facilitate easier insertion into or out of an introducer, depending in part on the direction the angled portion is facing. Any suitable number of fins may be disposed about the circumference of the lead attachment element 554 including, but not limited to, two, three, four, five, six, seven, eight, or more fins. The fins can be spaced apart uniformly or non-uniformly around the circumference of the lead attachment element 554.

This embodiment differs from the embodiments illustrated in FIGS. 3A, 3B, and 4 in that, instead of the fin extending straight (e.g., along a line that is parallel to a central axis extending along the center of the central lumen of the lead attachment element) along the exterior of the lead attachment element, each fin 551 extends from one end 570 to another end 571 along a line or curve that is not parallel to a central axis 549 of the central lumen 556 of the lead attachment element 554. In some embodiments, the fin 551 extends from one end 570 to the other end 571 is non-linear or curved arrangement. In some embodiments, the fins 551 are arranged along spiral paths along the lead attachment element 554, as illustrated in FIG. 5. In some embodiments, the fins 551 may also include additional curvature in the lateral direction away from the lead attachment element 554, as illustrate in FIG. 5.

The fins 551 are shown in FIG. 5 as extending along a full length of the lead attachment element 554, while being disposed about the circumference of the lead attachment element 554. However, in other embodiments, the fins 551 can extend along only a part (for example, 95%, 90%, 75%, 50%, or less) of the length of the lead attachment element 554.

The fins 551 are arranged to fold down and, at least in some embodiments, lie next to the lead attachment element 554 in a refracted position (not shown, but similar to the arrangement illustrated in FIG. 3B). FIG. 5 illustrates the outline of one fin 551' folded down and lying next to the lead attachment element 554 in the retracted position. In at least some embodiments, the fins 551 do not overlap each other when folded down into the retracted position. The retracted position is useful for implantation by delivery of the lead, with one or more anchoring units 550 attached, through an introducer, such as a needle, sheath, or cannula or any other suitable introducer. When the lead is inserted into the introducer, the fins 551 can fold down into the retracted position to reduce the overall diameter of the arrangement to no greater than the inner diameter of the introducer. In at least some embodiments, the fins 551 do not overlap to minimize or reduce the resulting diameter of the arrangement in the retracted position.

When the lead is implanted, the introducer is removed allowing the fins to extend into the deployed position, illustrated in FIG. 5. In at least some embodiments, the fins 551 are arranged to preferentially extend in the deployed position unless constrained by, for example, the introducer. In some embodiments, the fins 551 may be deployed into the deployed position, after withdrawal of the introducer, by rotating the lead (for example, by one quarter turn, one third turn, one half turn, or one full turn), pulling the lead backward, pushing the lead forward, or any combination of these movements or any other suitable movement (or combination of movements) of the lead. Alternatively, other methods or mechanisms for deploying the fins can also be used.

It will be recognized that a lead anchoring unit may include any combination of fins 351, fins 451, or fins 551. In at least some embodiments, when the fins 351, 451, 551 are in the retraction position, the fins do not overlap each other.

Figure 10A:
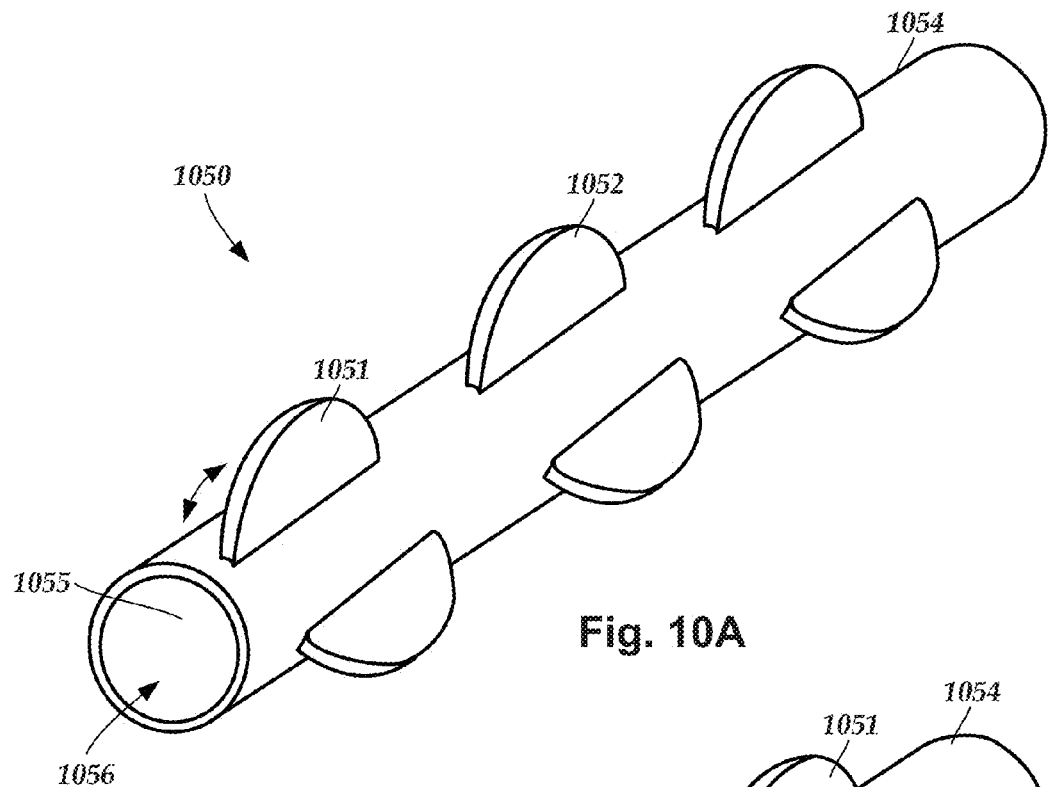
FIG. 10A is a schematic perspective view of a sixth embodiment of a lead anchoring unit in a deployed position, according to the invention.
Figure 10B:
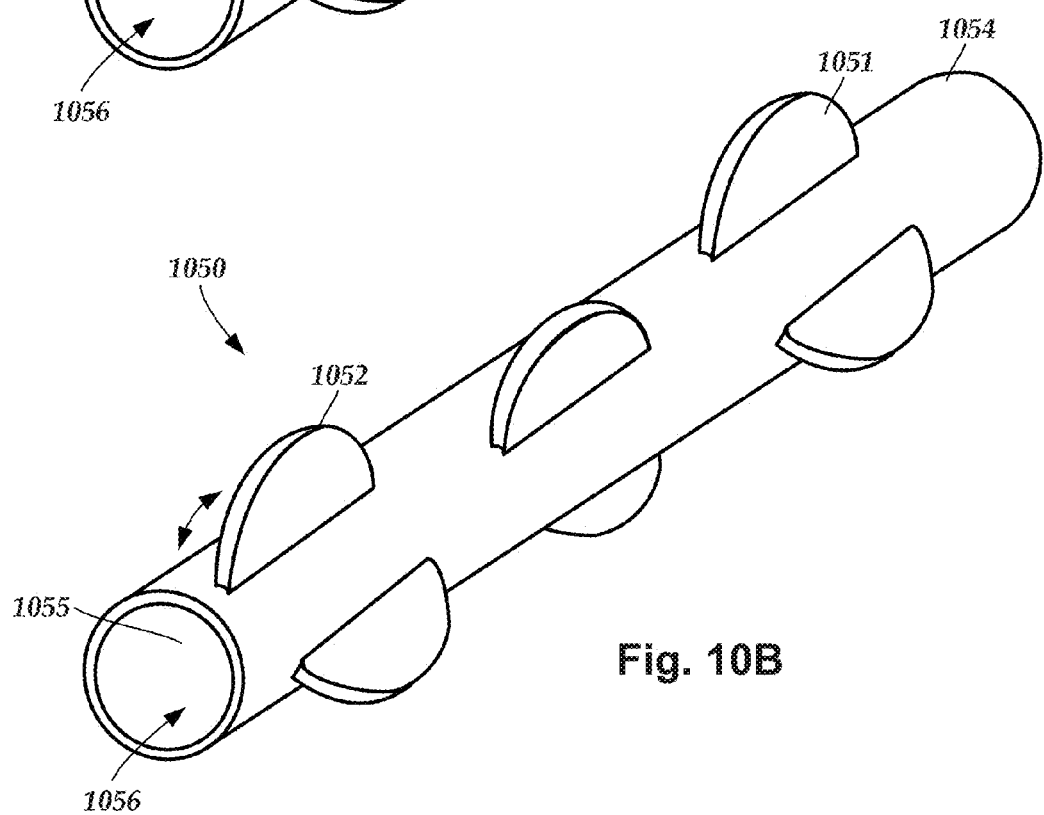
FIG. 10B is a schematic perspective view of a seventh embodiment of a lead anchoring unit in a deployed position, according to the invention.

FIG. 10A illustrates another embodiment of a lead anchoring unit 1050 that can be disposed along a distal end portion of a lead body (e.g., the lead body 106 as shown in FIG. 1). FIG. 10B illustrates an alternative embodiment of a lead anchoring unit 1050 that can be disposed along a distal end portion of a lead body (e.g., the lead body 106 as shown in FIG. 1). The lead anchoring unit facilitates anchoring the lead body to the surrounding tissue when implanted within a patient's body. The elements of lead anchoring unit 1050 are the same as similarly named elements of lead anchoring unit 350 except as described below.

The anchoring unit 1050 includes a lead attachment element 1054 having a tube-shaped (e.g., cylindrical) configuration. As shown, the lead attachment element 1054 has a central lumen 1056 extending along the length of the lead attachment element and having an interior surface 1055. The central lumen 1056 fits around at least a portion of the lead body of a lead. In at least some embodiments, the lead attachment element 1054 has a circular cross-section. However, the lead attachment element 1054 can be formed of any other suitable shape, including shapes having an elliptical, rectangular, polygonal, irregular, or any other suitable lateral cross-section. The lead attachment element 1054 can have a uniform lateral cross-section along its entire length or a varying lateral cross-section along its length. In at least some embodiments, the cross-section and dimensions of the lead attachment element 1054 are dictated by the configuration of the lead body. In at least some embodiments, the outer diameter of the lead body may be slightly larger than the diameter of the central lumen 1056 so that the lead attachment element fits snuggly on the lead body.

Figure 11A:
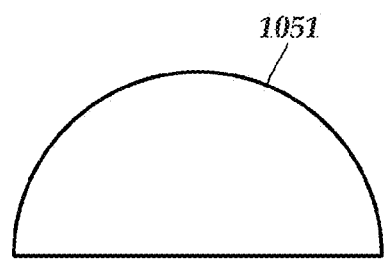
FIGS. 11A-11F are schematic side views of different anchoring fin shapes, according to the invention.
Figure 11B:
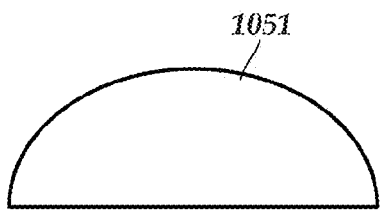
Figure 11C:
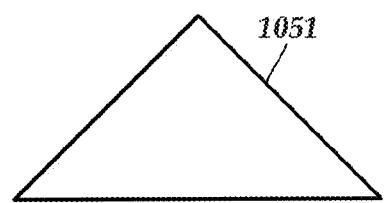
Figure 11D:
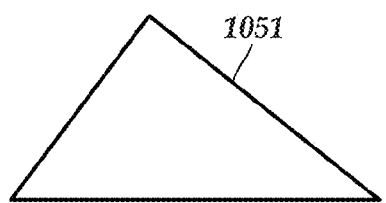
Figure 11E:
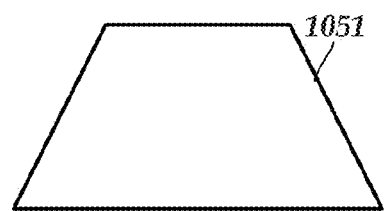
Figure 11F:
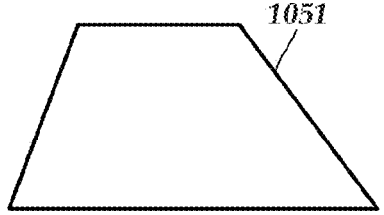

The anchoring unit 1050 includes at least one anchoring element 1052 coupled to the lead attachment element 1054. The anchoring element(s) 1052 are disposed around the lead attachment element 1054 and extend away from the lead attachment element 1054 when in a deployed position, as illustrated in FIG. 10A. In the illustrated embodiment, the anchoring elements 1052 are anchoring fins 1051. Any number of fins (or other anchoring elements) can be used. The embodiment shown in FIG. 10A includes three sets of three fins 1051 disposed about the circumference of the lead attachment element 1054 with each set disposed at a different longitudinal location along the lead attachment element. The fins 1051 shown in FIG. 10A have a half circular transverse cross-section, as illustrated in FIG. 11A, but it will be recognized that the fins 1051 can have any suitable shape including, but not limited to, half oval (FIG. 11B), isosceles triangle (FIG. 11C), non-isosceles triangle (FIG. 11D), symmetric or asymmetric trapezoid (FIGS. 11E and 11F), rectangle, regular, irregular, and the like. In at least some embodiments, the transverse cross-section of the fins 1051 is symmetric with respect to an axis perpendicular to the lead attachment element 1054 (see, for example, the fins 1051 of FIGS. 10A, 10B, 11A, 11B, 11C, and 11E.) The shape of the fins can facilitate easier insertion into or out of an introducer due to sloping of the fins in both directions. The shape of the fins 1051 provides anchoring to the lead to prevent or reduce movement or migration in both the anterior (forward) and posterior (rearward) directions.

Any suitable number of fins may be disposed about the circumference of the lead attachment element 1054 including, but not limited to, two, three, four, five, six, seven, eight, or more fins. The fins can be spaced apart uniformly or non-uniformly around the circumference of the lead attachment element 1054. In some embodiments, the fins 1051 can be provided in sets of two or more fins per set, with each set being disposed at a particular longitudinal position along the lead attachment element 1054 or lead with the fins of the set arranged at different circumferential positions. In the embodiments of FIGS. 10A and 10B, there are three sets of fins 1051. It will be understood that the anchoring units illustrated in FIGS. 3A-7B can also be modified to include multiple sets of fins or anchoring tabs similar to the distribution of fins 1051 in the embodiments of FIGS. 10A and 10B. In addition, it will be understood that the anchoring units 1050 can be arranged with a single set of fins 1051 similar to the anchoring units illustrated in FIGS. 3A-7B.

In at least some embodiments, the fins 1051 are arranged to fold down and, at least in some embodiments, lie next to the lead attachment element 1054 in a retracted position (not shown, but similar to the arrangement illustrated in FIG. 3B). The retracted position is useful for implantation by delivery of the lead, with one or more anchoring units 1050 attached, through an introducer, such as a needle, sheath, or cannula or any other suitable introducer. When the lead is inserted into the introducer, the fins 1051 can fold down into the retracted position to reduce the overall diameter of the arrangement to no greater than the inner diameter of the introducer. In at least some embodiments, the fins 1051 do not overlap to minimize or reduce the resulting diameter of the arrangement in the retracted position.

When the lead is implanted, the introducer is removed allowing the fins to extend into the deployed position, illustrated in FIGS. 10A and 10B. In at least some embodiments, the fins 1051 are arranged to preferentially extend in the deployed position unless constrained by, for example, the introducer. In some embodiments, the fins 1051 may be deployed into the deployed position, after withdrawal of the introducer, by rotating the lead (for example, by one quarter turn, one third turn, one half turn, or one full turn), pulling the lead backward, pushing the lead forward, or any combination of these movements or any other suitable movement (or combination of movements) of the lead. Alternatively, other methods or mechanisms for deploying the fins can also be used.

It will be recognized that a lead anchoring unit may include any combination of fins 351, fins 451, fins 551, or fins 1051. In at least some embodiments, when the fins 351, 451, 551, 1051 are in the retraction position, the fins do not overlap each other.

Figure 6A:
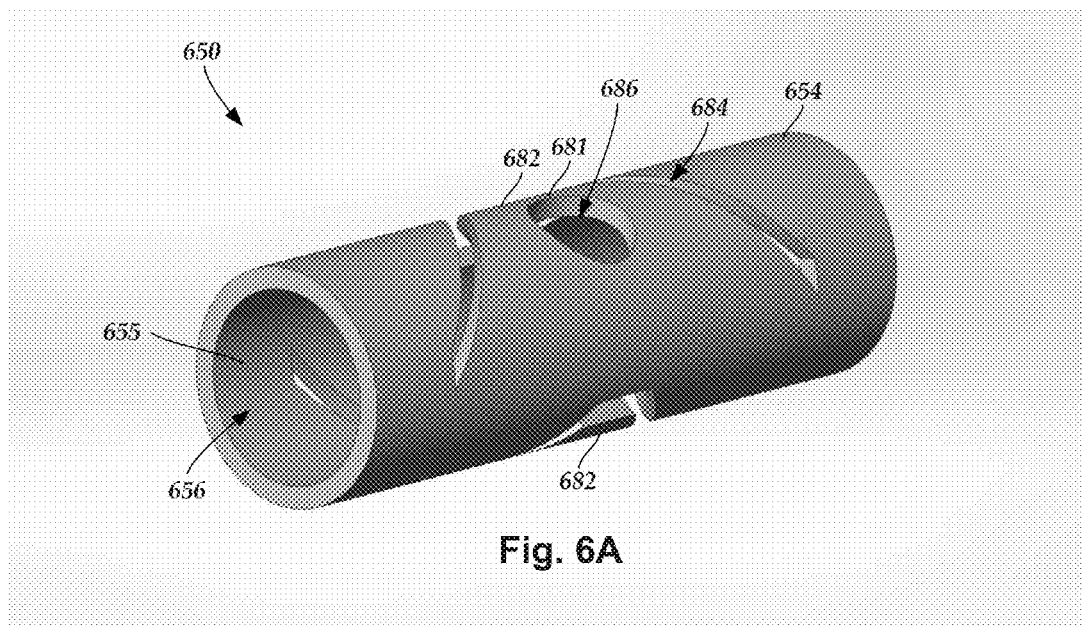
FIG. 6A is a schematic perspective view of a fourth embodiment of a lead anchoring unit in a retracted position, according to the invention.
Figure 6B:
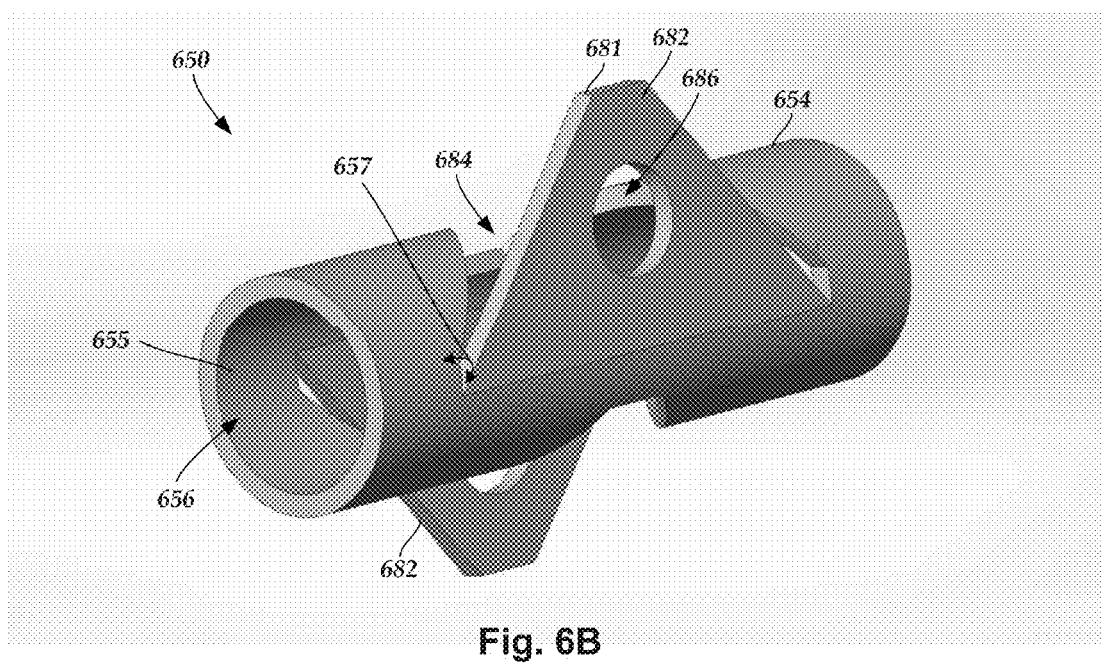
FIG. 6B is a schematic perspective view of the lead anchoring unit of FIG. 6A in a deployed position, according to the invention.

FIGS. 6A and 6B illustrate yet another embodiment of a lead anchoring unit 650 that can be disposed along a distal end portion of a lead body (e.g., the lead body 106 as shown in FIG. 1). The lead anchoring unit facilitates anchoring the lead body to the surrounding tissue when implanted within a patient's body. The elements of lead anchoring unit 650 are the same as similarly named elements of lead anchoring unit 350 except as described below.

The anchoring unit 650 includes a lead attachment element 654 having a tube-shaped (e.g., cylindrical) configuration. As shown, the lead attachment element 654 has a central lumen 656 extending along the length of the lead attachment element and having an interior surface 655. The central lumen 656 fits around at least a portion of the lead body of a lead. In at least some embodiments, the lead attachment element 654 has a circular cross-section. However, the lead attachment element 654 can be formed of any other suitable shape, including shapes having an elliptical, rectangular, polygonal, irregular, or any other suitable lateral cross-section. The lead attachment element 654 can have a uniform lateral cross-section along its entire length or a varying lateral cross-section along its length. In at least some embodiments, the cross-section and dimensions of the lead attachment element 654 are dictated by the configuration of the lead body. In at least some embodiments, the outer diameter of the lead body may be slightly larger than the diameter of the central lumen 656 so that the lead attachment element fits snuggly on the lead body.

The anchoring unit 650 defines at least one anchoring element 682 as part of the lead attachment element 654. The anchoring element(s) 682 are disposed around the lead attachment element 654 and extend away from the lead attachment element 654 when in a deployed position, as illustrated in FIG. 6B. In the illustrated embodiment, the anchoring elements 682 are anchoring tabs 681. Any number of tabs (or other anchoring elements) can be used. The embodiment shown in FIGS. 6A and 6B includes two tabs 681 disposed about the circumference of the lead attachment element 654. The tabs 681 in the embodiment of FIGS. 6A and 6B have the shape of an isosceles triangle with one apex cut off to form an isosceles trapezoid. It will be understood that the tabs can have any suitable shape including, but not limited to, trapezoidal, rectangular, hemispherical, regular, irregular, and the like. Any suitable number of tabs may be disposed about the circumference of the lead attachment element 654 including, but not limited to, one, two, three, four, five, six, seven, eight, or more tabs. The tabs can be spaced apart uniformly or non-uniformly around the circumference of the lead attachment element 654.

The tabs 681 are part of the lead attachment element 654 and defined, in part, by one or more cutouts 684 in the lead attachment element. The one or more cutouts can, for example, define all but one side of the tab 681 (for example, two, three, or four sides of the tab) and partially separate the tab from the lead attachment element 654. The cutouts can be formed, for example, during formation of the lead attachment element (e.g., by including the cutouts in a mold used to form the lead attachment element) or by laser or die cutting or any other suitable method.

In a retracted position, illustrated in FIG. 6A, the tabs 681 do not extend from the remainder of the lead attachment element 654. In some embodiments, the tabs 681 form a cylinder with the remainder of the lead attachment element 654. In a deployed position, illustrated in FIG. 6B, the tabs 681 extend away from the remainder of the lead attachment element 654 at an angle 657 so that they can extend into patient tissue. In some embodiments, the angle 657 is at least 15, 20, 30, 45, 60, 70, 80, or 90 degrees. In some embodiments, two tabs may be disposed opposite each other in the deployed position. The retracted position is useful for implantation by delivery of the lead, with one or more anchoring units 650 attached, through an introducer, such as a needle, sheath, or cannula or any other suitable introducer. When the lead is inserted into the introducer, the tabs 681 are in the retracted position to reduce the overall diameter of the arrangement.

When the lead is implanted, the introducer is removed allowing the tabs to extend into the deployed position, illustrated in FIG. 6B. In at least some embodiments, the tabs 681 are arranged to preferentially extend in the deployed position unless constrained by, for example, the introducer. Such tabs 681 may be biased toward the deployed position. In some embodiments, the tabs 681 may be placed in the deployed position and heat treated to prefer that position. In some embodiments, the tabs 681 may be deployed into the deployed position, after withdrawal of the introducer, by rotating the lead (for example, by one quarter turn, one third turn, one half turn, or one full turn) or any other suitable movement (or combination of movements) of the lead. In yet other embodiments, the tabs 681 can be formed of a material that assumes the deployed position when heated to body temperature. In these embodiments, the tabs 681 may accept or assume the retracted position at room temperature (for example, 20° C. or 25° C.) or when cooled to below room temperature (for example, 20° C. or lower, or 15° C. or lower) prior to implantation and then deploy into the deployed position when heated to body temperature (for example, above 30° C. or above 35° C.) by the surrounding patient tissue. Alternatively, other methods or mechanisms for deploying the tabs 681 can also be used.

The tabs 681 of the illustrated embodiment also include at least one opening 686 through the tab 681. This opening can allow tissue in-growth into or through the opening over time to further anchor the anchoring unit 650 within the patient tissue. In will be understood that such openings can also be added to any of the fins 351, 451, 551 described above and tabs 781 described below. In some embodiments, each tab or fin of an anchoring unit includes at least one opening. In other embodiments, one or more, but not all, of the tabs or fins of an anchoring unit include at least one opening.

Figure 7A:
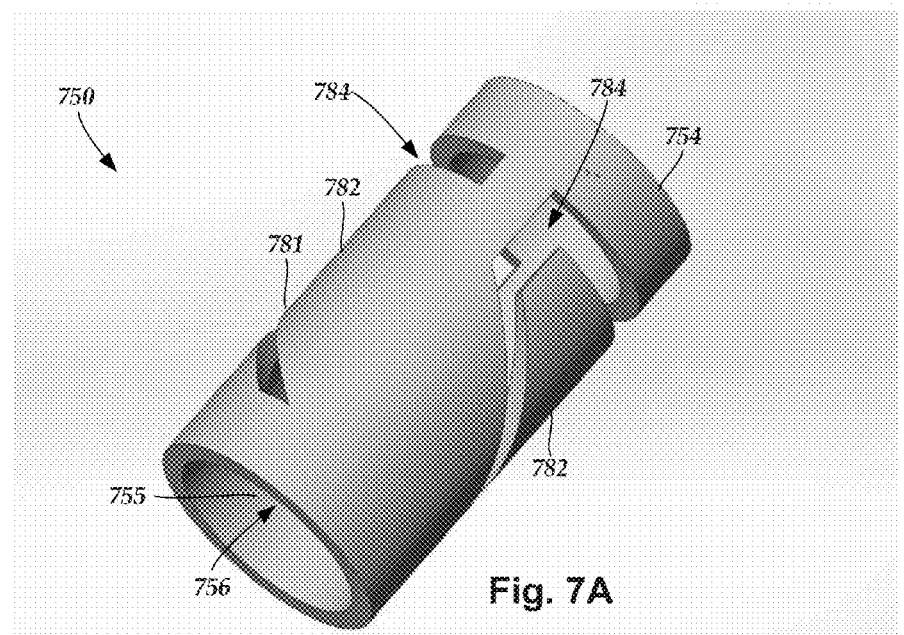
FIG. 7A is a schematic perspective view of a fifth embodiment of a lead anchoring unit in a retracted position, according to the invention.
Figure 7B:
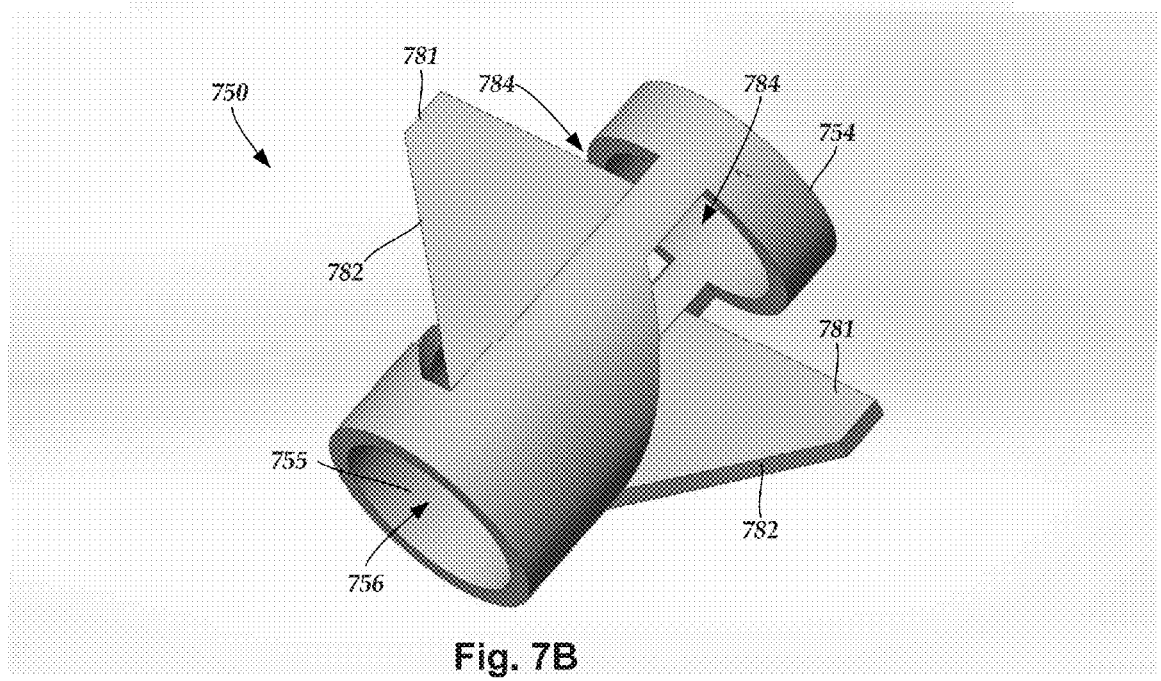
FIG. 7B is a schematic perspective view of the lead anchoring unit of FIG. 7A in a deployed position, according to the invention.

FIGS. 7A and 7B illustrate yet another embodiment of a lead anchoring unit 750 that can be disposed along a distal end portion of a lead body (e.g., the lead body 106 as shown in FIG. 1). The lead anchoring unit facilitates anchoring the lead body to the surrounding tissue when implanted within a patient's body. The elements of lead anchoring unit 750 are the same as similarly named elements of lead anchoring unit 350 or lead anchoring unit 650 except as described below.

The anchoring unit 750 includes a lead attachment element 754 having a tube-shaped (e.g., cylindrical) configuration. As shown, the lead attachment element 754 has a central lumen 756 extending along the length of the lead attachment element and having an interior surface 755. The central lumen 756 fits around at least a portion of the lead body of a lead. In at least some embodiments, the lead attachment element 754 has a circular cross-section. However, the lead attachment element 754 can be formed of any other suitable shape, including shapes having an elliptical, rectangular, polygonal, irregular, or any other suitable lateral cross-section. The lead attachment element 754 can have a uniform lateral cross-section along its entire length or a varying lateral cross-section along its length. In at least some embodiments, the cross-section and dimensions of the lead attachment element 754 are dictated by the configuration of the lead body. In at least some embodiments, the outer diameter of the lead body may be slightly larger than the diameter of the central lumen 756 so that the lead attachment element fits snuggly on the lead body.

The anchoring unit 750 defines at least one anchoring element 782 as part of the lead attachment element 754. The anchoring element(s) 782 are disposed around the lead attachment element 754 and extend away from the lead attachment element 754 when in a deployed position, as illustrated in FIG. 7B. In the illustrated embodiment, the anchoring elements 782 are anchoring tabs 781. Any number of tabs (or other anchoring elements) can be used. The embodiment shown in FIGS. 7A and 7B includes two tabs 781 disposed about the circumference of the lead attachment element 754. The tabs 781 in the embodiment of FIGS. 6A and 6B have the shape of a right triangle with one apex cut off to form a right trapezoid. It will be understood that the tabs can have any suitable shape including, but not limited to, trapezoidal, rectangular, hemispherical, regular, irregular, and the like. Any suitable number of tabs may be disposed about the circumference of the lead attachment element 754 including, but not limited to, one, two, three, four, five, six, seven, eight, or more tabs. The tabs can be spaced apart uniformly or non-uniformly around the circumference of the lead attachment element 754.

The tabs 781 are part of the lead attachment element 754 and defined, in part, by one or more cutouts 784 in the lead attachment element. The one or more cutouts can, for example, define all but one side of the tab 781 (for example, two, three, or four sides of the tab) and partially separate the tab from the lead attachment element 754. The cutouts can be formed, for example, during formation of the lead attachment element (e.g., by including the cutouts in a mold used to form the lead attachment element) or by laser or die cutting or any other suitable method.

In a retracted position, illustrated in FIG. 7A, the tabs 781 do not extend from the remainder of the lead attachment element 754. In some embodiments, the tabs 581 form a cylinder with the remainder of the lead attachment element 754. In a deployed position, illustrated in FIG. 7B, the tabs 781 extend away from the remainder of the lead attachment element 754 at an angle so that they can extend into patient tissue. In some embodiments, the angle is at least 15, 20, 30, 45, 60, 70, 80, or 90 degrees. In some embodiments, two tabs may be disposed opposite each other in the deployed position. The retracted position is useful for implantation by delivery of the lead, with one or more anchoring units 750 attached, through an introducer, such as a needle, sheath, or cannula or any other suitable introducer. When the lead is inserted into the introducer, the tabs 781 are in the retracted position to reduce the overall diameter of the arrangement.

When the lead is implanted, the introducer is removed allowing the tabs to extend into the deployed position, illustrated in FIG. 7B. In at least some embodiments, the tabs 781 are arranged to preferentially extend in the deployed position unless constrained by, for example, the introducer. Such tabs 781 may be biased toward the deployed position. In some embodiments, the tabs 781 may be placed in the deployed position and heat treated to prefer that position. In some embodiments, the tabs 781 may be deployed into the deployed position, after withdrawal of the introducer, by rotating the lead (for example, by one quarter turn, one third turn, one half turn, or one full turn) or any other suitable movement (or combination of movements) of the lead. In yet other embodiments, the tabs 781 can be formed of a material that assumes the deployed position when heated to body temperature. In these embodiments, the tabs 781 may accept or assume the retracted position at room temperature (for example, 20° C. or 25° C.) or when cooled to below room temperature (for example, 20° C. or lower, or 15° C. or lower) prior to implantation and then deploy into the deployed position when heated to body temperature (for example, above 30° C. or above 35° C.) by the surrounding patient tissue. Alternatively, other methods or mechanisms for deploying the tabs 781 can also be used. In at least some embodiments, the tabs 781 of the anchoring unit 750 can extend away from the lead attachment element 754 than the anchoring unit at a larger angle (relative to the retracted position) than the tabs 681 of the anchoring unit 650.

It will be understood that the anchoring units of FIGS. 6A-7B can be modified to including anchoring tabs that have shapes that are the same or similar to the shapes of the fins 1051 illustrated in FIGS. 10A-11F.

Figure 12:
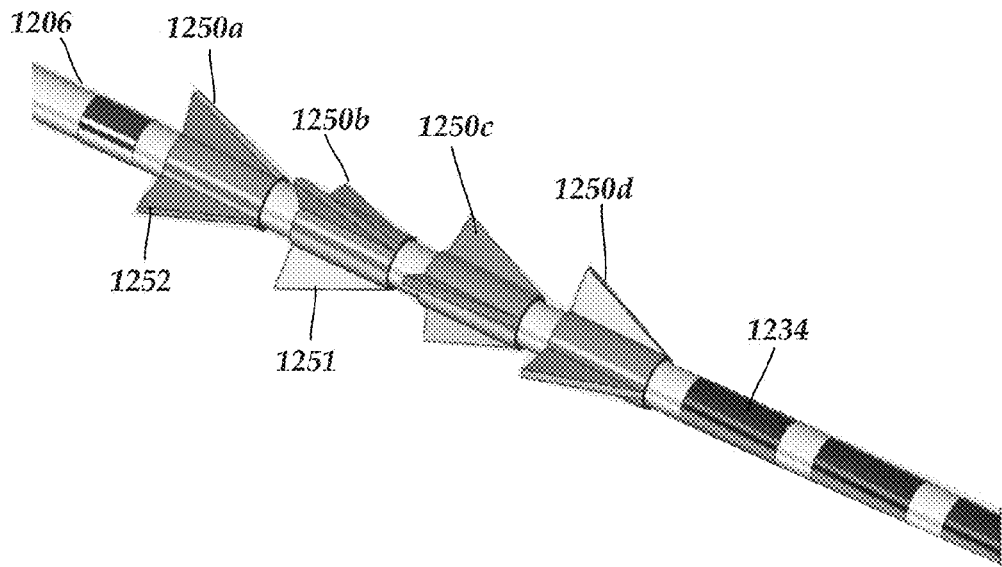
FIG. 12 is a schematic side view of another embodiment of a portion of a lead with lead anchoring units disposed between electrodes and with rotational staggering of the anchoring elements of adjacent anchoring units, according to the invention.

FIG. 12 illustrates another embodiment of a lead with a lead body 1206, electrodes 1234, and anchoring units 1250a-1250d. The elements of lead anchoring units 1250a-1250d are the same as similarly named elements of lead anchoring unit 350 except as described below.

In this embodiment, the anchoring elements 1252 (which are fins 1251 in this embodiment) of the anchoring units 1250a-1250d are rotationally staggered so that the anchoring elements of adjacent anchoring units are not longitudinally aligned but are rotationally offset from each other, as illustrated in FIG. 12. By rotationally staggering the anchoring elements of the anchoring units 1250a-1250d, more anchor surface area may be exposed to tissue in the event of lead migration. The rotational staggering may be by a uniform or non-uniform amount for each anchoring element or each anchoring unit. It will be understood that rotational staggering of the anchoring elements (e.g., fins or tabs) of the anchoring units can be applied to any of the other embodiments described herein including, but not limited to, the embodiments illustrated in FIGS. 3A-11F, 13, and 14.

FIG. 13 illustrates another embodiment of a lead with a lead body 1306, electrodes 1334, and anchoring units 1350a-1350d. The elements of lead anchoring units 1350a-1350d are the same as similarly named elements of lead anchoring unit 350 except as described below.

In this embodiment, the outer diameter (being the largest diameter of the anchoring unit perpendicular to the lead or lumen that receives the lead) of the anchoring elements 1352 (which in this embodiment are fins 1351) of the anchoring units 1350a-1350d decreases with the anchoring unit 1350a having the largest outer diameter and the anchoring unit 1350d having the smallest outer diameter. In this manner, the outer diameter or size of the anchoring elements 1352 of a set of anchoring units 1350a-1350d tapers (see dotted line 1349 of FIG. 13). In some embodiments, the set of anchoring units tapers (becomes smaller) from the proximal-most anchoring unit to the distal-most anchoring unit. It will be understood that the tapering may be uniform or non-uniform and may be monotonic or non-monotonic. It will be understood that tapering of the anchoring elements (e.g., fins or tabs) of the anchoring units can be applied to any of the other embodiments described herein including, but not limited to, the embodiments illustrated in FIGS. 3A-12 and 14.

FIG. 14 illustrates another embodiment of a lead with a lead body 1406, electrodes 1434, and anchoring units 1450a-1450d. The elements of lead anchoring units 1450a-1450d are the same as similarly named elements of lead anchoring unit 350 except as described below.

In this embodiment, the anchoring elements 1452 (which in this embodiment are fins 1451) of the anchoring units 1450a-1450d have a distal end that is curled rather than extending perpendicular or at an angle from the lead 1406. Curling of the distal end of the anchoring elements 1452 can reduce the outer dimension of the anchoring unit (i.e., the outer extent of the anchoring unit from the lead) while still presenting a substantial cross-section to the tissue to prevent or reduce lead migration. The curled distal end of the anchoring element 1452 does not lie next to the lead attachment element 1454 when deployed but is spaced apart from the lead attachment element 1454, as illustrated in FIG. 14. The curling of the distal end of the anchoring element 1452 may also aid in fitting within an introducer because the anchoring element 1452 is pre-curled and may more easily or consistently lie against the lead attachment element 1454.

In at least some embodiments, the anchoring elements 1452 can be curled by placing the lead with the anchoring units 1450a-1450d into a tube and twisting the tube to form the curl. While curled, the anchoring units can be heated to relax the plastic so that the curled configuration is the preferred deployed position of the anchoring elements. It will be understood that curling the distal end of the anchoring elements (e.g., fins or tabs) of the anchoring units can be applied to any of the other embodiments described herein including, but not limited to, the embodiments illustrated in FIGS. 3A-13.

Any of the anchoring units described herein can be formed of any suitable material, such as any suitable biocompatible material including, but not limited to, polymers, metals, alloys, or the like. In at least some embodiments, the anchoring unit is formed of silicone, polyurethane, or the like. In some embodiments, the material that is used has a stiffness that is sufficient to anchor the lead body to the surrounding tissue, while also having sufficient flexibility to reduce, or in some cases avoid, damage or injury to the tissue or to facilitate delivery of the lead with the anchoring unit(s) through an introducer.

Any of the anchoring units can be formed by any suitable manufacturing method including, but not limited to, molding, injection molding, extrusion, laser cutting, casting, or the like.

In some embodiments, the lead attachment element of any of the anchoring units described above is part of the lead body instead of being separate from the lead body as illustrated in FIGS. 3A-7B, 10A, 10B, and 12-14 so that it is disposed over a portion of the lead body. In these embodiments, the fins or tabs of the anchoring unit extend from the portion of the lead body which forms the lead attachment element. In these embodiments, the central lumen, if any, of the lead attachment element forms a part of the central lumen of the lead. In some embodiments, the fins can be molded with the lead body or can be attached to the lead body or can be formed using any other suitable method.

In some embodiments, the tabs can be cut from the lead body or molded with the lead body or can be formed using any other suitable method.

Figures 8A, 8B:
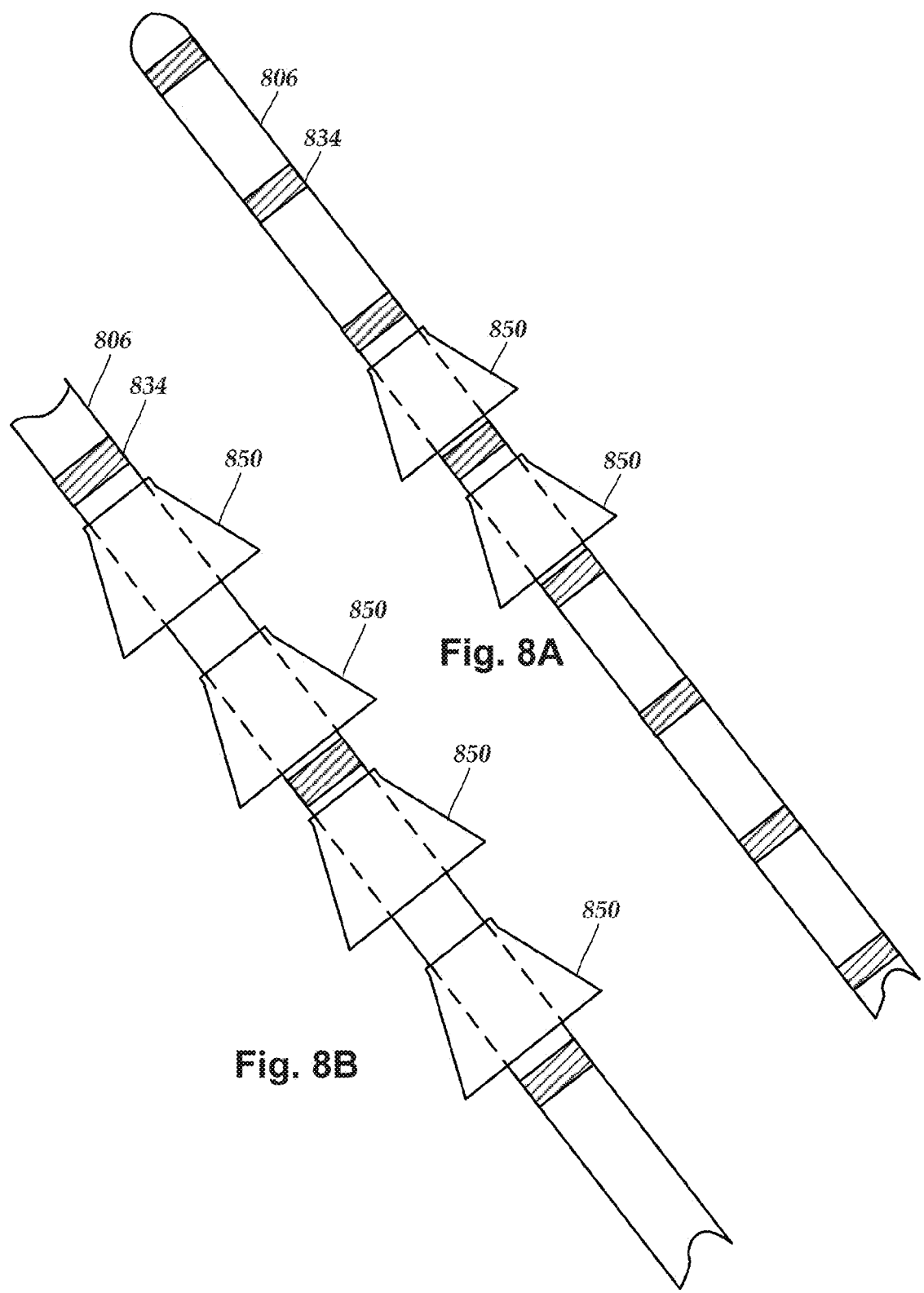
FIG. 8A is a schematic side view of one embodiment of a portion of a lead with lead anchoring units disposed between electrodes, according to the invention.
FIG. 8B is a schematic side view of another embodiment of a portion of a lead with lead anchoring units disposed between electrodes, according to the invention.

FIG. 8A is a schematic side view of one embodiment of a distal portion of a lead body 806, with lead anchoring units 850 disposed thereon. The distal portion of the lead body 806 includes multiple electrodes 834 spaced apart in a desired arrangement. In the embodiment of FIG. 8A, eight electrodes 834 are disposed on the lead body 806 in a uniform spaced apart arrangement, however, any suitable number of electrodes 834 can be provided in any suitable arrangement, including but not limited to two, four, eight, sixteen, or more electrodes. Examples of leads are described above with respect to FIGS. 1-2B and the references cited herein.

One or more anchoring units 850 are mounted on the lead body 806. In the illustrated embodiment, the anchoring units 850 are mounted between the electrodes 834, but it will be understood that other embodiments may include some or all of the anchoring units being mounted proximal to, or distal to, the electrodes or any combination thereof.

The anchoring units 850 may be any of the anchoring units describe above including the anchoring units 350, 450, 550, 650, 750, 1050, 1250*a*-1250*d*, 1350*a*-1350*d*, and 1450*a*-1450*d* of FIGS. 3A, 3B, 4, 5, 6A, 6B, 7A, 7B, 10A, 10B, and 12-14. In the embodiment shown in FIG. 8A, two anchoring units 850 are disposed over the lead body 806; however, any suitable number of anchoring units 850 may be used including one, two, three, four, five, six, seven, eight, nine, ten, or more anchoring units. The anchoring units may be all the same or there may be anchoring units of two or more different types (for examples, a combination of anchoring units 350 and anchoring units 450, a combination of anchoring units 350 and anchoring units 550, a combination of anchoring units 550 and anchoring units 450, a combination of anchoring units 350 and anchoring units 650, a combination of anchoring units 550 and anchoring units 750, and so forth.)

A variety of methods may be employed to attach the anchoring unit 850 to the lead body 806. For example, each individual anchoring unit 850 can be slid onto the lead body 806 to the desired position along the lead body. In some embodiments, an annular depression in the lead body may be made to receive the anchoring unit.

In some embodiments, the anchoring unit 850 is swelled prior to sliding on the lead body. As an example, a silicone anchoring unit 850 can be treated with a heptane solution to swell the anchoring unit so that it can be slid onto the lead body. As the heptane evaporates, the anchoring unit 850 will return to its original dimensions. In other embodiments, the anchoring unit 850 is otherwise stretched or expanded (for example, using pins or the like) and slid onto the lead body.

In some embodiments, the anchoring unit 850 includes a longitudinal slit so that it can be placed on the lead body by opening the slit to receive the lead body into the central lumen of the anchoring unit.

In some embodiments, the anchoring unit 850 is made of a heat shrink material so that it can be slid onto the lead body in its original form and then shrunk using heat to the desired final shape. In some embodiments, the anchoring unit 850 is molded or overmolded onto the lead body.

In some embodiments, the anchoring unit 850 may form a friction fit with the lead body to hold the anchoring unit in place. In some embodiments, an adhesive, such as a silicone adhesive, may be employed to bond the anchoring unit 850 to the lead body. In other embodiments, the anchoring unit 850 is formed of a heat shrinkable material that, once the anchoring unit 850 is in place, is shrunk to fix the anchoring unit on the lead body. In some embodiments, the anchoring unit 850, lead body, or both are heated to cause flowing of the heated material and then subsequently cooled to bond the anchoring unit to the lead body. In other embodiments, a mechanical locking arrangement can be used such as, for example, bosses, bumps, or the like in the lead body or the anchoring unit can engage holes in the anchoring unit or lead body. Any other suitable method or any combination of the described methods can be used to fix the anchoring unit to the lead body.

FIG. 8B is a schematic side view of another embodiment of a distal portion of a lead body 806, with lead anchoring units 850 disposed thereon. In contrast to the embodiment shown in FIG. 8A, the embodiment of FIG. 8B includes two anchoring units 850 disposed between a pair of electrodes 834. In this embodiment, the two anchoring units 850 may be spaced apart from each other. Although FIG. 8 shows two anchoring units, any suitable number of anchoring units 850 may be disposed between a pair of electrodes 834. In some embodiments, two or more different types of anchoring units 850 are employed to provide enhanced tissue anchorage, as indicated above. As an example, the anchoring unit 350 shown in FIGS. 3A and 3B and the anchoring unit 450 shown in FIG. 4 can both be disposed between a pair of electrodes 834. In another example, the anchoring unit 350 shown in FIGS. 3A and 3B and the anchoring unit 650 shown in FIGS. 6A and 6B can both be disposed between a pair of electrodes 834.

Additional arrangements of anchoring units, which can be used to arrange any of the anchoring units (or combination thereof) described herein can be found at U.S. Provisional Patent Application Ser. Nos. 61/823,240; 61/970,649; and 61/947,126, all of which are incorporated herein by reference.

Figure 9:
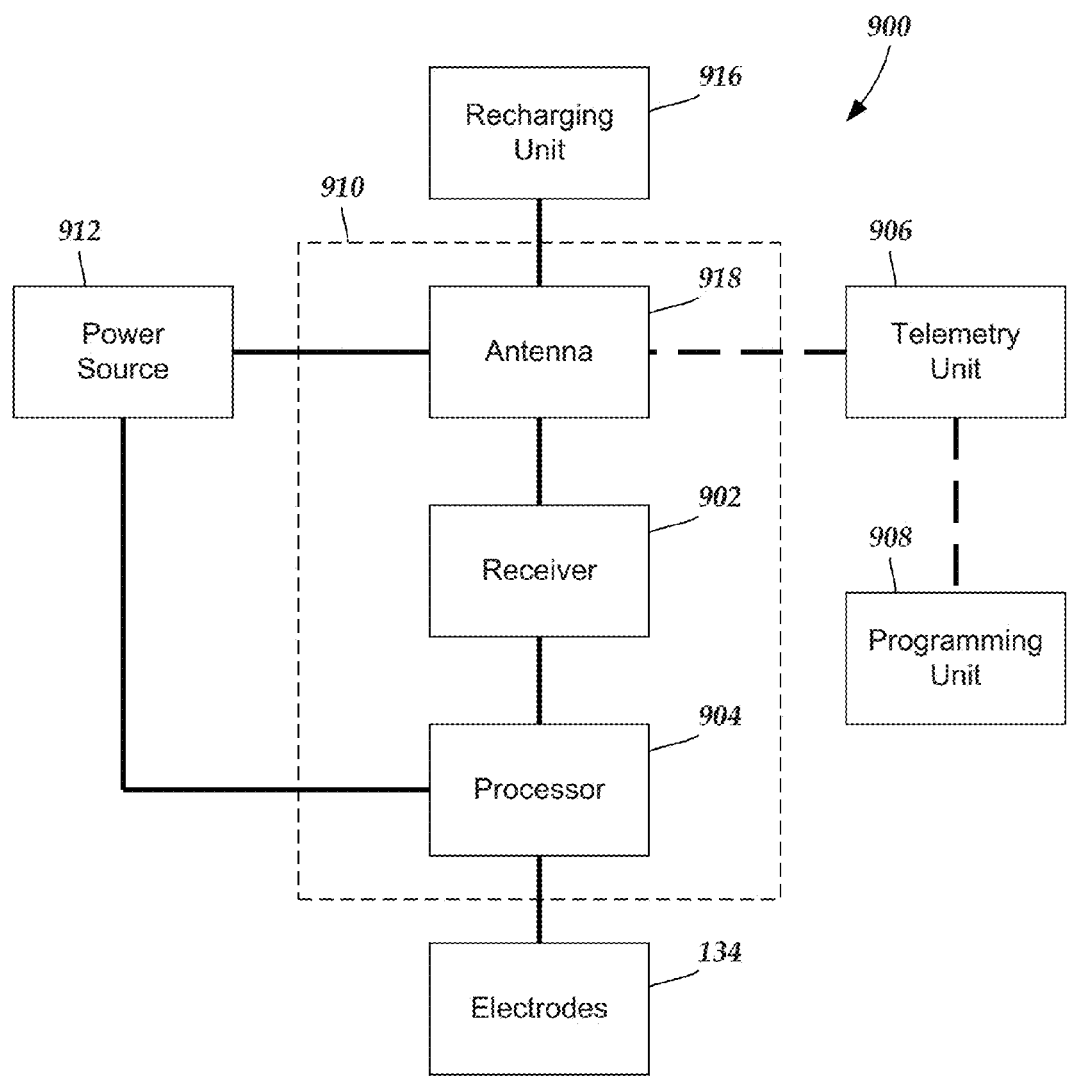
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, a power source 912, an antenna 918, a receiver 902, and a processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 selects which electrode(s) are cathodes and which electrode(s) are anodes. In some embodiments, the processor 904 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by the programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and the receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include the antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation lead, comprising:
   a non-conductive lead body having an outer surface, a distal end portion, a proximal end portion, and a longitudinal length;
   a plurality of electrodes disposed along the distal end portion of the lead body;
   a plurality of terminals disposed along the proximal end portion of the lead body;
   a plurality of conductors extending through the lead body, each conductor of the plurality of conductors electrically coupling each of the plurality of terminals to at least one of the plurality of electrodes; and
   at least one anchoring unit disposed around the outer surface of a portion of the lead body, each of the at least one anchoring unit having a first end and a second end and comprising
      a lead attachment element having a longitudinal length and a central lumen within which a portion of the lead body is received, and
      a plurality of anchoring fins, wherein each anchoring fin is attached to the lead attachment element and each anchoring fin extends away from the lead attachment element when in a deployed position and is configured and arranged for contact with patient tissue to anchor the lead within the patient tissue, wherein each anchoring fin is configured and arranged to have a retracted position in which the anchoring fin folds down and lies next to the lead attachment element and does not overlap with any other of the plurality of anchoring fins in the retracted position, wherein each of the anchoring fins is attached to the lead attachment element along at least 90% of the longitudinal length of the lead attachment element.

2. The electrical stimulation lead of claim 1, wherein each anchoring fin increases in size from the first end to the second end of the at least one anchoring unit to which it is attached or each anchoring fin has a curled distal end.

3. The electrical stimulation lead of claim 1, wherein each anchoring fin has a first side and wherein, in the deployed position, the first side of at least one of the anchoring tins forms an angle with the lead attachment element of less than 90 degrees so that the anchoring fin preferentially folds down with the first side next to the lead attachment element.

4. The electrical stimulation lead of claim 1, wherein the central lumen of the lead attachment element defines a central axis and wherein at least one of the anchoring fins has a first end and a second end and extends from the first end to the second end of the anchoring fin along a line of attachment between the anchoring fin and the lead attachment element that is not parallel to the central axis of the central lumen.

5. The electrical stimulation lead of claim 1, wherein at least one of the anchoring fins has a first end and a second end and extends along a line of attachment between the anchoring fin and the lead attachment element from the first end to the second end of the anchoring fin along a non-linear curve.

6. The electrical stimulation lead of claim 1, wherein each of the anchoring fins is coupled in a curved attachment line between the anchoring fin and the lead attachment element.

7. The electrical stimulation lead of claim 1, wherein at least one of the anchoring fins comprises an opening through the anchoring fin to allow tissue in-growth through the opening.

8. The electrical stimulation lead of claim 1, wherein the at least one anchoring unit is a plurality of anchoring units and wherein either the anchoring fins of adjacent anchoring units are rotationally staggered or an outer diameter of the anchoring fins decreases between adjacent anchoring units.

9. An electrical stimulation system, comprising:
the electrical stimulation lead of claim 1;
a control module coupleable to the electrical stimulation lead, the control module comprising
a housing, and
an electronic subassembly disposed in the housing; and
a connector for receiving the electrical stimulation lead, the connector having a proximal end, a distal end, and a longitudinal length, the connector comprising
a connector housing defining a port at the distal end of the connector, the port configured and arranged for receiving the proximal end portion of the lead body of the electrical stimulation lead, and
a plurality of connector contacts disposed in the connector housing, the plurality of connector contacts configured and arranged to couple to at least one of the plurality of terminals disposed along the proximal end portion of the lead body of the electrical stimulation lead.

10. An electrical stimulation lead, comprising:
a non-conductive lead body having an outer surface, a distal end portion, a proximal end portion, and a longitudinal length;
a plurality of electrodes disposed along the distal end portion of the lead body;
a plurality of terminals disposed along the proximal end portion of the lead body;
a plurality of conductors extending through the lead body, each conductor of the plurality of conductors electrically coupling each of the plurality of terminals to at least one of the plurality of electrodes; and
at least one anchoring unit disposed around the outer surface of a portion of the lead body, each of the at least one anchoring unit having a first end and a second end and comprising
a lead attachment element defining at least one anchoring tab and a central lumen within which the portion of the lead body is received, wherein each anchoring tab is partially separated from a remainder of the lead attachment element by at least one cutout, wherein each anchoring tab extends away from the remainder of the lead attachment element when in a deployed position and is configured and arranged for contact with patient tissue to anchor the lead within the patient tissue, wherein each anchoring tab is configured and arranged to have a retracted position in which the at least one anchoring tab form a cylindrical arrangement with the remainder of the lead attachment element.

11. The electrical stimulation lead of claim 10, wherein at least one of the at least one anchoring tab has an isosceles trapezoidal shape in the deployed position.

12. The electrical stimulation lead of claim 10, wherein at least one of the at least one anchoring tab has a right trapezoidal shape in the deployed position.

13. The electrical stimulation lead of claim 10, wherein the at least one anchoring tab comprises a first anchoring tab and a second anchoring tab opposite the first anchoring tab when both the first and second anchoring tabs are in the deployed position.

14. The electrical stimulation lead of claim 10, wherein the at least one anchoring tab is configured and arranged to deploy when heated within a body of a patient upon implantation.

15. The electrical stimulation lead of claim 10, wherein, in the deployed position, the at least one anchoring tab extends at an angle of at least 30 degrees with respect to the remainder of the lead attachment element.

16. The electrical stimulation lead of claim 10, Wherein the at least one anchoring tab is configured and arranged to deploy when the lead is rotated within a body of a patient after implantation.

17. The electrical stimulation lead of claim 10, wherein at least one of the at least one anchoring tab comprises an opening through the anchoring tab to allow tissue in-growth through the opening.

18. An electrical stimulation system, comprising:
the electrical stimulation lead of claim 10;
a control module coupleable to the electrical stimulation lead, the control module comprising
a housing, and
an electronic subassembly disposed in the housing; and
a connector for receiving the electrical stimulation lead, the connector having a proximal end, a distal end, and a longitudinal length, the connector comprising
a connector housing defining a port at the distal end of the connector, the port configured and arranged for receiving the proximal end portion of the lead body of the electrical stimulation lead, and
a plurality of connector contacts disposed in the connector housing, the plurality of connector contacts configured and arranged to couple to at least one of the plurality of terminals disposed on the proximal end portion of the lead body of the electrical stimulation lead.

* * * * *